United States Patent
Hermens et al.

(10) Patent No.: US 10,865,423 B2
(45) Date of Patent: *Dec. 15, 2020

(54) VECTORS WITH MODIFIED INITIATION CODON FOR THE TRANSLATION OF AAV-REP78 USEFUL FOR PRODUCTION OF AAV

(71) Applicant: uniQure IP B.V., Amsterdam (NL)

(72) Inventors: Wilhelmus Theodorus Johannes Maria Christiaan Hermens, Amsterdam (NL); Saskia Jacoba Petronella Haast, Huizen (NL); Dennis Johan Biesmans, Weesp (NL); Andrew Christian Bakker, Almere (NL)

(73) Assignee: uniQure IP B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/739,914

(22) Filed: Jan. 10, 2020

(65) Prior Publication Data

US 2020/0131535 A1 Apr. 30, 2020

Related U.S. Application Data

(60) Continuation of application No. 16/179,648, filed on Nov. 2, 2018, now Pat. No. 10,533,188, which is a continuation of application No. 15/978,669, filed on May 14, 2018, now Pat. No. 10,138,496, which is a division of application No. 15/424,560, filed on Feb. 3, 2017, now Pat. No. 9,988,645, which is a continuation of application No. 14/603,469, filed on Jan. 23, 2015, now Pat. No. 9,708,627, which is a continuation of application No. 13/945,505, filed on Jul. 18, 2013, now Pat. No. 8,952,144, which is a division of application No. 12/306,239, filed as application No. PCT/NL2007/050298 on Jun. 20, 2007, now Pat. No. 8,512,981.

(60) Provisional application No. 60/815,262, filed on Jun. 21, 2006.

(30) Foreign Application Priority Data

Jun. 21, 2006 (EP) .................................... 06115804

(51) Int. Cl.
| | | |
|---|---|---|
| *C12N 7/00* | (2006.01) | |
| *C12N 15/86* | (2006.01) | |
| *C07K 14/005* | (2006.01) | |
| *A61K 48/00* | (2006.01) | |
| *C12N 15/00* | (2006.01) | |

(52) U.S. Cl.
CPC ............ *C12N 15/86* (2013.01); *C07K 14/005* (2013.01); *C12N 7/00* (2013.01); *C12N 2710/14043* (2013.01); *C12N 2710/14044* (2013.01); *C12N 2710/14143* (2013.01); *C12N 2710/14144* (2013.01); *C12N 2710/14152* (2013.01); *C12N 2750/14121* (2013.01); *C12N 2750/14122* (2013.01); *C12N 2750/14143* (2013.01); *C12N 2750/14151* (2013.01); *C12N 2750/14152* (2013.01); *C12N 2800/105* (2013.01); *C12N 2800/50* (2013.01)

(58) Field of Classification Search
CPC ...................... C12N 15/86; C12N 7/00; C12N 2750/14143; C12N 2710/14143; C07K 14/005

See application file for complete search history.

(56) References Cited

U.S. PATENT DOCUMENTS

| | | |
|---|---|---|
| 2003/0148506 A1 | 8/2003 | Kotin et al. |
| 2004/0197895 A1 | 10/2004 | Kotin et al. |

FOREIGN PATENT DOCUMENTS

| | | |
|---|---|---|
| WO | WO-99/61641 A1 | 12/1999 |
| WO | WO-2005/072364 A2 | 8/2005 |

OTHER PUBLICATIONS

Cecchini et al., "Toward exascale production of recombinant adeno-associated virus for gene transfer applications", Gene Therapy, 15:823-830 (2008) (Nature Publishing Group) (8 pages).

Kohlbrenner et al., "Successful Production of Pseudotyped rAA V Vectors Using a Modified Baculovirus Expression System" Molecular Therapy, 12:1217-1225 (2005) (The Amer. Soc. of Gene Therapy) (9 pages).

Negrete et al., "Strategies for manufacturing recombinant adeno-associated virus vectors for gene exploiting baculovirus technology" Brief Funct Genomic Proteomic. 7: 303-311 (2008) (Author manuscript, NIH Public Access) (also published by Oxford Journals) (14 pages).

(Continued)

*Primary Examiner* — Barry A Chestnut
(74) *Attorney, Agent, or Firm* — Foley & Lardner LLP; Sunit Talapatra

(57) ABSTRACT

The present invention relates nucleic acid constructs for the production of recombinant parvoviral (e.g. adeno-associated viral) vectors in insect cells, to insect cells comprising such constructs and to methods wherein the cells are used to produce recombinant parvoviral virions. The insect cells preferably comprise a first nucleotide sequence encoding the parvoviral rep proteins whereby the initiation codon for translation of the parvoviral Rep78 protein is a suboptimal initiation codon that effects partial exon skipping upon expression in insect cells. The insect cell further comprises a second nucleotide sequence comprising at least one parvoviral (AAV) inverted terminal repeat (ITR) nucleotide sequence and a third nucleotide sequence comprising a sequences coding for the parvoviral capsid proteins.

15 Claims, 5 Drawing Sheets
Specification includes a Sequence Listing.

(56) References Cited

OTHER PUBLICATIONS

Oranje et al., "423. Isolation of Adeno-Associated Virus (AAV)-Specific Camelid-Derived Single Chain Antibody Fragment: A Novel Tool for Purification of AAV Vectors of Different Serotypes", Molecular Therapy, vol. 9, Iss. S1, (Abstr. 423) 2004 (1 page).

Redemann et al., "Adeno-Associated Virus Rep Protein Synthesis during Productive Infection" Journal of Virology, Feb. 1989, 63:873-882 (10 pages).

Smith et al., "A Simplified Baculovirus-AAV Expression Vector System Coupled With One-step Affinity Purification Yields High-titer rAAV Stocks From Insect Cells", Molecular Therapy 17:1888-1896 (Nov. 2009) (The American Society of Gene & Cell Therapy) (9 pages).

Urabe et al., "Insect Cells as a Factory to Produce Adeno-Associated Virus Type 2 Vectors", Human Gene Therapy, 13:135-1943 (Nov. 2002) (Mary Ann Liebert, Inc.) (23 pages).

16 hours post infection:

40 hours post infection:

64 hours post infection:

VECTORS WITH MODIFIED INITIATION CODON FOR THE TRANSLATION OF AAV-REP78 USEFUL FOR PRODUCTION OF AAV

CROSS-REFERENCE TO RELATED APPLICATIONS

This application is a Continuation of Application of U.S. patent application Ser. No. 16/179,648, filed Nov. 2, 2018, which is a Continuation Application of U.S. patent application Ser. No. 15/978,669, filed May 14, 2018, now U.S. Pat. No. 10,138,496, which is a Divisional Application of U.S. patent application Ser. No. 15/424,560, filed Feb. 3, 2017, now U.S. Pat. No. 9,988,645, which is a Continuation Application of U.S. patent application Ser. No. 14/603,469, filed Jan. 23, 2015, now U.S. Pat. No. 9,708,627, which is a Continuation Application of U.S. patent application Ser. No. 13/945,505, filed Jul. 18, 2013, now U.S. Pat. No. 8,952,144, which is a Divisional Application of U.S. patent application Ser. No. 12/306,239, filed Dec. 22, 2008, now U.S. Pat. No. 8,512,981, which is the National Phase of International Patent Application No. PCT/NL2007/050298, filed Jun. 20, 2007, and published on Dec. 27, 2007 as WO/2007/148971 A1, which claims priority to European Patent Application No. 06115804.4, filed Jun. 21, 2006, which claims priority to U.S. Provisional Application No. 60/815,262, filed Jun. 21, 2006. The contents of these applications are herein incorporated by reference in their entirety.

The instant application contains a Sequence Listing which has been submitted in ASCII format via EFS-WEB and is hereby incorporated by reference in its entirety. Said ASCII copy, created on May 3, 2018, is named 069818-2522Sequence.txt and is 17 KB.

FIELD OF THE INVENTION

The present invention relates to the production of adeno-associated vims in insect cells and to adeno-associated vims with improvements in expression and stability of the viral rep proteins that increase the productivity of adeno-associated viral vectors in insect cells.

BACKGROUND OF THE INVENTION

Adeno-associated vims (AAV) may be considered as one of the most promising viral vectors for human gene therapy. AAV has the ability to efficiently infect dividing as well as non-dividing human cells, the AAV viral genome integrates into a single chromosomal site in the host cell's genome, and most importantly, even though AAV is present in many humans it has never been associated with any disease. In view of these advantages, recombinant adeno-associated vims (rAAV) is being evaluated in gene therapy clinical trials for hemophilia B, malignant melanoma, cystic fibrosis, and other diseases.

Host cells that sustain AAV replication in vitro are all derived from mammalian cell types. Therefore, rAAV for use in gene therapy has thus far mainly been produced on mammalian cell lines such as e.g. 293 cells, COS cells, HeLa cells, KB cells, and other mammalian cell lines (see e.g. U.S. Pat. Nos. 6,156,303, 5,387,484, 5,741,683, 5,691,176, 5,688,676, US 20020081721, WO 00/47757, WO 00/24916, and WO 96/17947). rAAV vectors are typically produced in such mammalian cell culture systems by providing DNA plasmids that contain the therapeutic gene flanked by the origin of AAV replication (inverted terminal repeats or ITRs), genes for AAV replication proteins Rep78, Rep68, Rep52, and Rep40, and genes for virion or structural proteins VP1, VP2, and VP3. In addition, a plasmid containing early genes from adenovims (E2A, E40RF6, VARNA) is provided to enhance the expression of the AAV genes and improve vector yield (see e.g. Grimm et al., 1998, Hum. Gene Ther. 9:2745-2760). However, in most of these mammalian cell culture systems, the number of AAV particles generated per cell is on the order of $10^4$ particles (reviewed in Clark, 2002, Kidney Int. 61 (Suppl. 1):9-15). For a clinical study, more than $10^{15}$ particles of rAAV may be required. To produce this number of rAAV particles, transfection and culture with approximately $10^{11}$ cultured human 293 cells, the equivalent of 5,000 175-$cm^2$ flasks of cells, would be required, which means transfecting up to $10^{11}$ 293 cells. Therefore, large scale production of rAAV using mammalian cell culture systems to obtain material for clinical trials has already proven to be problematic, production at commercial scale may not even be feasible. Furthermore there is always the risk, that a vector for clinical use that is produced in a mammalian cell culture will be contaminated with undesirable, perhaps pathogenic, material present in the mammalian host cell.

To overcome these problems of mammalian productions systems, recently, an AAV production system has been developed using insect cells (Urabe et al., 2002, Hum. Gene Ther. 13:I9354 943; US 20030148506 and US 2004OI97895). For production of AAV in insect cells some modifications were necessary in order to achieve the correct stoichiometry of the three AAV capsid proteins (VPI, VP2 and VP3), which relies on a combination of alternate usage of two splice acceptor sites and the suboptimal utilization of an ACG initiation codon for VP2 that is not accurately reproduced by insect cells. To mimic the correct stoichiometry of the capsid proteins in insect cells Urabe et al. (2002, supra) use a construct that is transcribed into a single polycistronic messenger that is able to express all three VP proteins without requiring splicing and wherein the most upstream initiator codon is replaced by the suboptimal initiator codon ACG. In co-pending application (PCT/NL2005/050018) the present inventors have further improved the infectivity of baculovirus-produced rAAV vectors based production by further optimisation of the stoichiometry of AAV capsid proteins in insect cells.

For expression of the AAV Rep proteins in the AAV insect cell expression system as initially developed by Urabe et al. (2002, supra), a recombinant baculovirus construct is used that harbours two independent Rep expression units (one for Rep78 and one for Rep52), each under the control of a separate insect cell promoter, the MEI and PolH promoters, respectively. In this system, the MEI promoter, a much weaker promoter than the PolH promoter, was chosen for driving Rep78 expression since it is known that in mammalian cells a less abundant expression of Rep78 as compared to Rep52 favours high vector yields (Li et al., 1997, J Virol. 7I:5236-43; Grimm et al., I 998, supra).

More recently however, Kohlbrenner et al. (2005, Mol. Ther. 12:12I 7-25) reported that the baculovirus construct for expression of the two Rep protein, as used by Urabe et al., suffers from an inherent instability. By splitting the palindromic orientation of the two Rep genes in Urabe's original vector and designing two separate baculovirus vectors for expressing Rep52 and Rep78, Kohlbrenner et al. (2005, supra) increased the passaging stability of the vector. However, despite the consistent expression of Rep78 and Rep52 from the two independent baculovirus-Rep constructs in insect cells over at least 5 passages, rAAV vector yield is 5 to 10-fold lower as compared to the original baculovirus-Rep construct designed by Urabe et al. (2002, supra).

There is thus still a need to overcome the above serious limitations of large scale (commercial) production of AAV vectors in insect cells. Thus it is an object of the present invention to provide for means and methods that allow for stable and high yield (large scale) production of AAV vectors in insect cells.

DESCRIPTION OF THE INVENTION

Definitions

As used herein, the term "operably linked" refers to a linkage of polynucleotide (or polypeptide) elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

"Expression control sequence" refers to a nucleic acid sequence that regulates the expression of a nucleotide sequence to which it is operably linked. An expression control sequence is "operably linked" to a nucleotide sequence when the expression control sequence controls and regulates the transcription and/or the translation of the nucleotide sequence. Thus, an expression control sequence can include promoters, enhancers, internal ribosome entry sites (IRES), transcription terminators, a start codon in front of a protein-encoding gene, splicing signal for introns, and stop codons. The term "expression control sequence" is intended to include, at a minimum, a sequence whose presence are designed to influence expression, and can also include additional advantageous components. For example, leader sequences and fusion partner sequences are expression control sequences. The term can also include the design of the nucleic acid sequence such that undesirable, potential initiation codons in and out of frame, are removed from the sequence. It can also include the design of the nucleic acid sequence such that undesirable potential splice sites are removed. It includes sequences or polyadenylation sequences (pA) which direct the addition of a polyA tail, i.e., a string of adenine residues at the 3'-end of a mRNA, sequences referred to as polyA sequences. It also can be designed to enhance mRNA stability. Expression control sequences which affect the transcription and translation stability, e.g., promoters, as well as sequences which effect the translation, e.g., Kozak sequences, are known in insect cells. Expression control sequences can be of such nature as to modulate the nucleotide sequence to which it is operably linked such that lower expression levels or higher expression levels are achieved.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer. A "tissue specific" promoter is only active in specific types of tissues or cells.

The terms "substantially identical", "substantial identity" or "essentially similar" or "essential similarity" means that two peptide or two nucleotide sequences, when optimally aligned, such as by the programs GAP or BESTFIT using default parameters, share at least a certain percentage of sequence identity as defined elsewhere herein. GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). It is clear than when RNA sequences are said to be essentially similar or have a certain degree of sequence identity with DNA sequences, thymine (T) in the DNA sequence is considered equal to uracil (U) in the RNA sequence. Sequence alignments and scores for percentage sequence identity may be determined using computer programs, such as the GCG Wisconsin Package, Version 10.3, available from Accelrys Inc., 9685 Scranton Road, San Diego, Calif. 92121 USA or the open-source software Emboss for Windows (current version 2.7.1-07). Alternatively percent similarity or identity may be determined by searching against databases such as FASTA, BLAST, etc.

Nucleotide sequences encoding parvoviral Rep proteins of the invention may also be defined by their capability to hybridise with the nucleotide sequence of SEQ ID NO.10, respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridization conditions in order to specifically identify sequences varying in identity between 50% and 90%.

DETAILED DESCRIPTION OF THE INVENTION

The present invention relates the use of animal parvoviruses, in particular dependoviruses such as infectious human or simian AAV, and the components thereof (e.g., an animal parvovirus genome) for use as vectors for introduction and/or expression of nucleic acids in mammalian cells. In particular, the invention relates to improvements in productivity of such parvoviral vectors when produced in insect cells.

Viruses of the Parvoviridae family are small DNA animal viruses. The family Parvoviridae may be divided between two subfamilies: the Parvovirinae, which infect vertebrates, and the Densovirinae, which infect insects. Members of the subfamily Parvovirinae are herein referred to as the parvoviruses and include the genus Dependovirus. As may be deduced from the name of their genus, members of the Dependovirus are unique in that they usually require coinfection with a helper virus such as adenovirus or herpes virus for productive infection in cell culture. The genus Dependovirus includes AAV, which normally infects humans (e.g., serotypes 1, 2, 3A, 3B, 4, 5, and 6) or primates (e.g., serotypes 1 and 4), and related viruses that infect other warm-blooded animals (e.g., bovine, canine, equine, and ovine adeno-associated viruses). Further information on parvoviruses and other members of the Parvoviridae is described in Kenneth I. Berns, "Parvoviridae: The Viruses and Their Replication," Chapter 69 in Fields Virology (3d Ed. 1996). For convenience the present invention is further exemplified and described herein by reference to AAV. It is however understood that the invention is not limited to AAV but may equally be applied to other parvoviruses.

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1,-2 and -3) form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wtAAV infection in mammalian cells the Rep genes (i.e. Rep78 and Rep52) are expressed from the P5 promoter and the P19 promotor, respectively and both Rep proteins have a function in the replication of the viral genome. A splicing event in the Rep ORF results in the expression of actually four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

A "recombinant parvoviral or AAV vector" (or "rAAV vector") herein refers to a vector comprising one or more polynucleotide sequences of interest, genes of interest or "Transgenes" that are flanked by parvoviral or AAV inverted terminal repeat sequences (ITRs). Such rAAV vectors can be replicated and packaged into infectious viral particles when present in an insect host cell that is expressing AAV rep and cap gene products (i.e. AAV Rep and Cap proteins). When an rAAV vector is incorporated into a larger nucleic acid construct (e.g. in a chromosome or in another vector such as a plasmid or baculovirus used for cloning or transfection), then the rAAV vector is typically referred to as a "pro-vector" which can be "rescued" by replication and encapsidation in the presence of AAV packaging functions and necessary helper functions.

In a first aspect the invention relates to a nucleotide sequence comprising an open reading frame comprising nucleotide sequences encoding animal parvoviruses Rep proteins, wherein the initiation codon for translation of the parvoviral Rep78 protein is a suboptimal initiation codon. The suboptimal initiation codon preferably is an initiation codon that effects partial exon skipping. Partial exon skipping is herein understood to mean that at least part of the ribosomes do not initiate translation at the suboptimal initiation codon of the Rep78 protein but at an initiation codon further downstream, whereby preferably the initiation codon further downstream is the initiation codon of the Rep52 protein. The suboptimal initiation codon preferably effects partial exon skipping upon expression of the nucleotide sequence in an insect cell. Preferably, the suboptimal initiation codon effects partial exon skipping in an insect cell so as to produce in the insect cell a molar ratio of Rep78 to Rep52 in the range of 1:10 to 10:1, 1:5 to 5:1, or 1:3 to 3:1, preferably at about 20-40 hours post infection, more preferably at about 30-40 hours post infection, using a baculovirus expression. The molar ration of the Rep78 and Rep52 may be determined by means of Western blotting as described in Example 1.1.3, preferably using a monoclonal antibody that recognizes a common epitope of both Rep78 and Rep52, or using the antibody described in Example 1.1.3.

The term "suboptimal initiation codon" herein not only refers to the tri-nucleotide initiation codon itself but also to its context. Thus, a suboptimal initiation codon may consist of an "optimal" ATG codon in a suboptimal context, e.g. a non-Kozak context. However, more preferred are suboptimal initiation codons wherein the tri-nucleotide initiation codon itself is suboptimal, i.e. is not ATG. Suboptimal is herein understood to mean that the codon is less efficient in the initiation of translation in an otherwise identical context as compared to the normal ATG codon. Preferably, the efficiency of suboptimal codon is less than 90, 80, 60, 40 or 20% of the efficiency of the normal ATG codon in an otherwise identical context. Methods for comparing the relative efficiency of initiation of translation are known per se to the skilled person. Preferred suboptimal initiation codons may be selected from ACG, TTG, CTG, and GTG. More preferred is ACG.

A nucleotide sequence encoding animal parvoviruses Rep proteins, is herein understood as a nucleotide sequence encoding the non-structural Rep proteins that are required and sufficient for parvoviral vector production in insect cells such the Rep78 and Rep52 proteins. The animal parvovirus nucleotide sequence preferably is from a dependovirus, more preferably from a human or simian adeno-associated virus (AAV) and most preferably from an AAV which normally infects humans (e.g., serotypes 1, 2, 3A, 3B, 4, 5, and 6) or primates (e.g., serotypes 1 and 4). An example of a nucleotide sequence encoding animal parvoviruses Rep proteins is given in SEQ ID No.IO, which depicts a part of the AAV serotype-2 sequence genome encoding the Rep proteins. The Rep78 coding sequence comprises nucleotides 11-1876 and the Rep52 coding sequence comprises nucleotides 683-1876. It is understood that the exact molecular weights of the Rep78 and Rep52 proteins, as well as the exact positions of the translation initiation codons may differ between different parvoviruses. However, the skilled person will know how to identify the corresponding position in nucleotide sequence from other parvoviruses than AAV-2. A nucleotide sequence encoding animal parvoviruses Rep proteins may thus also be defined as a nucleotide sequence:

a) that encodes a polypeptide comprising an amino acid sequence that has at least 50, 60, 70, 80, 88, 89, 90, 95, 97, 98, or 99% sequence identity with the amino acid sequence of SEQ ID NO. 11;

b) that has at least 50, 60, 70, 80, 81, 82, 85, 90, 95, 97, 98, or 99% sequence identity
with the nucleotide sequence of positions 11-1876 of SEQ ID NO. 10;

c) the complementary strand of which hybridises to a nucleic acid molecule sequence of or (b);

d) nucleotide sequences the sequence of which differs from the sequence of a nucleic acid molecule of (c) due to the degeneracy of the genetic code.

Preferably, the nucleotide sequence encodes animal parvoviruses Rep proteins that are required and sufficient for parvoviral vector production in insect cells.

A further preferred nucleotide sequence of the invention comprises an expression control sequence that comprising a nine nucleotide sequence of SEQ. ID NO:7 or a nucleotide sequence substantially homologous to SEQ. ID NO:7, upstream of the initiation codon of the nucleotide sequence encoding the parvoviral Rep78 protein. A sequence with substantial identity to the nucleotide sequence of SEQ. ID NO:7 and that will help increase expression of the parvoviral Rep78 protein is e.g. a sequence which has at least 60%, 70%, 80% or 90% identity to the nine nucleotide sequence of SEQ ID NO:7.

Elimination of possible false translation initiation sites in the Rep protein coding sequences, other than the Rep78 and Rep52 translation initiation sites, of other parvoviruses will be well understood by an artisan of skill in the art, as will be the elimination of putative splice sites that may be recognized in insect cells. The various modifications of the wild-type parvoviral sequences for proper expression in insect cells is achieved by application of well-known genetic engineering techniques such as described e.g. in Sambrook and Russell (2001) "Molecular Cloning: A Laboratory Manual (3rd edition), Cold Spring Harbor Laboratory, Cold Spring Harbor Laboratory Press, New York. Various further modifications of Rep protein coding regions are known to the skilled artisan which could increase yield of Rep protein. These modifications are within the scope of the present invention.

In a further aspect the invention relates to a nucleic acid construct comprising a nucleotide sequence encoding parvoviral Rep proteins as defined above. Preferably, in the construct, the nucleotide sequence encoding the parvoviral Rep proteins is operably linked to expression control sequences for expression in an insect cell. These expression control sequences will at least include a promoter that is active in insect cells. Techniques known to one skilled in the art for expressing foreign genes in insect host cells can be used to practice the invention. Methodology for molecular engineering and expression of polypeptides in insect cells is described, for example, in Summers and Smith. 1986. A Manual of Methods for Baculovirus Vectors and Insect Culture Procedures, Texas Agricultural Experimental Station Bull. No. 7555, College Station, Tex.; Luckow. 1991. In Prokop et al., Cloning and Expression of Heterologous Genes in Insect Cells with Baculovirus Vectors' Recombinant DNA Technology and Applications, 97-152; King, L. A. and R. D. Possee, 1992, The baculovirus expression system, Chapman and Hall, United Kingdom; O'Reilly, D. R., L. K. Miller, V. A. Luckow, 1992, Baculovirus Expression Vectors: A Laboratory Manual, New York; W. H. Freeman and Richardson, C. D., 1995, Baculovirus Expression Protocols, Methods in Molecular Biology, volume 39; U.S. Pat. No. 4,745,051; US2003148506; and WO 03/074714. A particularly suitable promoter for transcription of the nucleotide sequence of the invention encoding of the parvoviral Rep proteins is e.g. the polyhedron promoter. However, other promoters that are active in insect cells are known in the art, e.g. the p10, p35, IE-1 or ΔIE-1 promoters and further promoters described in the above references.

Preferably the nucleic acid construct for expression of the parvoviral Rep proteins in insect cells is an insect cell-compatible vector. An "insect cell-compatible vector" or "vector" is understood to a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cells genome but the presence of the vector in the insect cell need not be permanent and transient episomal vectors are also included. The vectors can be introduced by any means known, for example by chemical treatment of the cells, electroporation, or infection. In a preferred embodiment, the vector is a baculovirus, a viral vector, or a plasmid. In a more preferred embodiment, the vector is a baculovirus, i.e. the construct is a baculoviral vector. Baculoviral vectors and methods for their use are described in the above cited references on molecular engineering of insect cells.

In another aspect the invention relates to an insect cell that comprises no more than one type of nucleotide sequence comprising a single open reading frame encoding a parvoviral Rep protein. Preferably the single open reading frame encodes one or more of the parvoviral Rep proteins, more preferably the open reading frame encodes all of the parvoviral Rep proteins, most preferably the open reading frame encodes the full-length Rep 78 protein from which preferably at least both Rep 52 and Rep 78 proteins may be expressed in the insect cell. It is understood herein that the insect cell may comprise more than one copy of the single type of nucleotide sequence, e.g. in a multicopy episomal vector, but that these are multiple copies of essentially one and the same nucleic acid molecule, or at least nucleic acid molecules that encode one and the same Rep amino acid sequence, e.g. nucleic acid molecules that only differ between each other due to the degeneracy of the genetic code. The presence of only a single type of nucleic acid molecule encoding the parvoviral Rep proteins avoids recombination between homologous sequences as may be present in different types of vectors comprising Rep sequences, which may give rise to defective Rep expression constructs that affect (stability of) parvoviral production levels in insect cells. Preferably, in the insect cell, the nucleotide sequence comprising the single open reading frame encoding one or more parvoviral Rep proteins is part of a nucleic acid construct wherein the nucleotide sequence is operably linked to expression control sequences for expression in an insect cell. A further preferred insect cell comprises as a "first" nucleotide sequence a nucleotide sequence as defined above encoding parvoviral Rep proteins, preferably a coding sequence with a suboptimal initiation codon as defined above, or a nucleic acid construct as defined above or the insect cell comprises as a "first" nucleic acid construct a nucleic acid construct as defined above comprising such nucleotide sequences.

Any insect cell which allows for replication of a recombinant parvoviral (rAAV) vector and which can be maintained in culture can be used in accordance with the present invention. For example, the cell line used can be from *Spodoptera frugiperda*, drosophila cell lines, or mosquito cell lines, e.g., *Aedes albopictus* derived cell lines. Preferred insect cells or cell lines are cells from the insect species which are susceptible to baculovirus infection, including e.g. Se301, SeIZD2109, SeUCR1, Sf9, Sf900+, Sf21, BTI-TN-5B1-4, MG-1, Tn368, HzAm1, Ha2302, Hz2E5, High Five (Invitrogen, CA, USA) and expresSF+® (U.S. Pat. No. 6,103,526; Protein Sciences Corp., CT, USA).

A preferred insect cell according to the invention, in addition to the above described "first" nucleotide sequence or a nucleic acid construct, further comprises:
 a) a second nucleotide sequence comprising at least one parvoviral inverted terminal repeat (ITR) nucleotide sequence; and,
 b) a third nucleotide sequence comprising parvoviral Cap protein coding sequences operably linked to expression control sequences for expression in an insect cell.

In the context of the invention "at least one parvoviral ITR nucleotide sequence" is understood to mean a palindromic sequence, comprising mostly complementary, symmetrically arranged sequences also referred to as "A," "B," and "C" regions. The ITR functions as an origin of replication, a site having a "cis" role in replication, i.e., being a recognition site for transacting replication proteins such as e.g. Rep 78 (or Rep68) which recognize the palindrome and specific sequences internal to the palindrome. One exception to the symmetry of the ITR sequence is the "D" region of the ITR. It is unique (not having a complement within one ITR). Nicking of single-stranded DNA occurs at the junction between the A and D regions. It is the region where new DNA synthesis initiates. The D region normally sits to one side of the palindrome and provides directionality to the nucleic acid replication step. An parvovirus replicating in a mammalian cell typically has two ITR sequences. It is, however, possible to engineer an ITR so that binding sites are on both strands of the A regions and D regions are located symmetrically, one on each side of the palindrome. On a double-stranded circular DNA template (e.g., a plasmid), the Rep78- or Rep68-assisted nucleic acid replication then proceeds in both directions and a single ITR suffices for parvoviral replication of a circular vector. Thus, one ITR nucleotide sequence can be used in the context of the present invention. Preferably, however, two or another even number of regular ITRs are used. Most preferably, two ITR sequences are used. A preferred parvoviral ITR is an AAV ITR. For safety reasons it may be desirable to construct a recombinant parvoviral (rAAV) vector that is unable to further propagate after initial introduction into a cell. Such a safety mechanism for limiting undesirable vector propagation in a recipient may be provided by using rAAV with a chimeric ITR as described in US2003148506.

The number of nucleic acid constructs employed in the insect cell for the production of the recombinant parvoviral (rAAV) vector is not limiting in the invention. For example, one, two, three, four, five, or more separate constructs can be employed to produce rAAV in insect cells in accordance with the methods of the present invention. If five constructs are employed, one construct encodes AAV VP 1, another construct encodes AAV VP2, yet another construct encodes AAV VP3, still yet another construct encodes the Rep protein as defined above and a final construct comprises at least one AAV ITR. If fewer than five constructs are used, the constructs can comprise various combinations of the at least one AAV ITR and the VP1, VP2, VP3, and the Rep protein coding sequences. Preferably, two constructs or three constructs are used, with two constructs being more preferred as described above. If two constructs are used, preferably the insect cell comprises: (a) a first nucleic acid construct for expression of the Rep proteins as defined above, which construct further comprises the third nucleotide sequences as defined in (b) above (comprising parvoviral Cap protein coding sequences operably linked to at least one expression control sequence for expression in an insect cell; see also below); and (c) a second nucleic acid construct comprising the second nucleotide sequence as defined in (a) above (comprising at least one parvoviral/AAV ITR nucleotide sequence). If three constructs are used, preferably the same configuration as used for two constructs is used except that separate constructs are used for expression of the capsid proteins and for expression of the Rep proteins. The sequences on each construct can be in any order relative to each other. For example, if one construct comprises ITRs and an ORF comprising nucleotide sequences encoding VP capsid proteins, the VP ORF can be located on the construct such that, upon replication of the DNA between ITR sequences, the VP ORF is replicated or not replicated. For another example, the Rep coding sequences and/or the ORF comprising nucleotide sequences encoding VP capsid proteins can be in any order on a construct. It is understood that also the second, third and further nucleic acid construct(s) preferably are an insect cell-compatible vectors, preferably a baculoviral vectors as described above. Alternatively, in the insect cell of the invention, one or more of the first nucleotide sequence, second nucleotide sequence, third nucleotide sequence, and fourth nucleotide sequence and optional further nucleotide sequences may be stably integrated in the genome of the insect cell. One of ordinary skill in the art knows how to stably introduce a nucleotide sequence into the insect genome and how to identify a cell having such a nucleotide sequence in the genome. The incorporation into the genome may be aided by, for example, the use of a vector comprising nucleotide sequences highly homologous to regions of the insect genome. The use of specific sequences, such as transposons, is another way to introduce a nucleotide sequence into a genome.

In the invention, the third nucleotide sequence comprising parvoviral capsid (Cap) protein coding sequences is herein understood to comprises sequences encoding each of the three parvoviral capsid proteins, VP1, -2 and -3. The third nucleotide sequence comprising the capsid protein coding sequences may be present in various forms. E.g. separate coding sequences for each of the capsid proteins VP1, -2 and -3 may used, whereby each coding sequence is operably linked to expression control sequences for expression in an insect cell. More preferably, however, the third nucleotide sequence comprises a single open reading frame encoding all three of the animal parvoviral (AAV) VP1, VP2, and VP3 capsid proteins, wherein the initiation codon for translation of the VP1 capsid protein is a suboptimal initiation codon that is not ATG as e.g. described by Urabe et al. (2002, supra). A suboptimal initiation codon for the VP1 capsid protein may be as defined above for the Rep78 protein. More preferred suboptimal initiation codons for the VP1 capsid protein may be selected from ACG, TTG, CTG and GTG, of which CTG and GTG are most preferred. A preferred third nucleotide sequence for the expression of the capsid proteins further comprises an expression control sequence comprising a nine nucleotide sequence of SEQ. ID NO:7 or a nucleotide sequence substantially homologous to SEQ. ID NO:7, upstream of the initiation codon of the nucleotide sequence encoding the VP1 capsid protein. A sequence with substantial identity to the nucleotide sequence of SEQ. ID NO:7 and that will help increase expression of VP1 is e.g. a sequence which has at least 60%, 70%, 80% or 90% identity to the nine nucleotide sequence of SEQ ID NO:7. A further preferred third nucleotide sequence for expression of the capsid proteins further preferably comprises at least one modification of the nucleotide sequence encoding the VP 1 capsid protein selected from among a C at nucleotide position 12, an A at nucleotide position 21, and a C at nucleotide position 24 (with reference to position 1 being the first nucleotide of the translation initiation codon; see SEQ ID NO.I). Elimination of possible false initiation codons for translation of VP1 of other serotypes will be well understood by an artisan of skill in the art, as will be the elimination of putative splice sites that may be recognised in insect cells. Various further modifications of VP coding regions are known to the skilled artisan which could either increase yield of VP and virion or have other desired effects, such as altered tropism or reduce antigenicity of the virion. These modifications are within the scope of the present invention. Preferably the nucleotide sequence of the invention encoding the parvoviral capsid proteins is operably linked to expression control sequences for expression in an insect cell, which will at least include a promoter that is active in insect cells. Such control sequences and further techniques and materials (e.g. vectors) for expressing parvoviral capsid proteins in insect host cells are already described above for the Rep proteins.

In a preferred embodiment of the invention, the second nucleotide sequence present in the insect cells of the invention, i.e. the sequence comprising at least one parvoviral (AAV) ITR, further comprises at least one nucleotide sequence encoding a gene product of interest, whereby preferably the at least one nucleotide sequence encoding a gene product of interest becomes incorporated into the genome of a recombinant parvoviral (rAAV) vector produced in the insect cell. Preferably, at least one nucleotide sequence encoding a gene product of interest is a sequence for expression in a mammalian cell. Preferably, the second nucleotide sequence comprises two parvoviral (AAV) ITR nucleotide sequences and wherein the at least one nucleotide sequence encoding a gene product of interest is located between the two parvoviral (AAV) ITR nucleotide sequences. Preferably, the nucleotide sequence encoding a gene product of interest (for expression in the mammalian cell) will be incorporated into the recombinant parvoviral (rAAV) vector produced in the insect cell if it is located between two regular ITRs, or is located on either side of an ITR engineered with two D regions.

The second nucleotide sequence defined herein above may thus comprise a nucleotide sequence encoding at least one "gene product of interest" for expression in a mammalian cell, located such that it will be incorporated into an recombinant parvoviral (rAAV) vector replicated in the insect cell. Any nucleotide sequence can be incorporated for later expression in a mammalian cell transfected with the recombinant parvoviral (rAAV) vector produced in accordance with the present invention. The nucleotide sequence may e.g. encode a protein it may express an RNAi agent, i.e. an RNA molecule that is capable of RNA interference such as e.g. a shRNA (short hairpinRNA) or an siRNA (short interfering RNA). "siRNA" means a small interfering RNA that is a short-length double-stranded RNA that are not toxic in mammalian cells (Elbashir et al., 2001, Nature 411:494-98; Caplen et al., 2001, Proc. Natl. Acad. Sci. USA 98:9742-47). In a preferred embodiment, the second nucleotide sequence may comprise two nucleotide sequences and each encodes one gene product of interest for expression in a mammalian cell. Each of the two nucleotide sequences encoding a product of interest is located such that it will be incorporated into a recombinant parvoviral (rAAV) vector replicated in the insect cell.

The product of interest for expression in a mammalian cell may be a therapeutic gene product. A therapeutic gene product can be a polypeptide, or an RNA molecule (siRNA), or other gene product that, when expressed in a target cell, provides a desired therapeutic effect such as e.g. ablation of an undesired activity, e.g. the ablation of an infected cell, or the complementation of a genetic defect, e.g. causing a deficiency in an enzymatic activity. Examples of therapeutic polypeptide gene products include CFTR, Factor IX, Lipoprotein lipase (LPL, preferably LPL S447X; see WO 01/00220), Apolipoprotein Al, Uridine Diphosphate Glucuronosyltransferase (UGT), Retinitis Pigmentosa GTPase Regulator Interacting Protein (RP-GRIP), and cytokines or interleukins like e.g. IL-10.

Alternatively, or in addition as a second gene product, second nucleotide sequence defined herein above may comprise a nucleotide sequence encoding a polypeptide that serve as marker proteins to assess cell transformation and expression. Suitable marker proteins for this purpose are e.g. the fluorescent protein GFP, and the selectable marker genes HSV thymidine kinase (for selection on HAT medium), bacterial hygromycin B phosphotransferase (for selection on hygromycin B), Tn5 aminoglycoside phosphotransferase (for selection on G418), and dihydrofolate reductase (DHFR) (for selection on methotrexate), CD20, the low affinity nerve growth factor gene. Sources for obtaining these marker genes and methods for their use are provided in Sambrook and Russel (2001) "Molecular Cloning: A Laboratory Manual (3rd edition), Cold Spring Harbor Laboratory, Cold Spring Harbor Laboratory Press, New York. Furthermore, second nucleotide sequence defined herein above may comprise a nucleotide sequence encoding a polypeptide that may serve as a fail-safe mechanism that allows to cure a subject from cells transduced with the recombinant parvoviral (rAAV) vector of the invention, if deemed necessary. Such a nucleotide sequence, often referred to as a suicide gene, encodes a protein that is capable of converting a prodrug into a toxic substance that is capable of killing the transgenic cells in which the protein is expressed. Suitable examples of such suicide genes include e.g. the *E. coli* cytosine deaminase gene or one of the thymidine kinase genes from Herpes Simplex Virus, Cytomegalovirus and Varicella-Zoster virus, in which case ganciclovir may be used as prodrug to kill the transgenic cells in the subject (see e.g. Clair et al., 1987, Antimicrob. Agents Chemother. 31:844-849).

In another embodiment one of the gene products of interest can be an AAV protein. In particular, a Rep protein, such as Rep78 or Rep68, or a functional fragment thereof. A nucleotide sequence encoding a Rep78 and/or a Rep68, if present on the genome of a recombinant parvoviral (rAAV) vector of the invention and expressed in a mammalian cell transduced with the vector, allows for integration of the recombinant parvoviral (rAAV) vector into the genome of the transduced mammalian cell. Expression of Rep78 and/or Rep68 in an rAAV-transduced or infected mammalian cell can provide an advantage for certain uses of the recombinant parvoviral (rAAV) vector, by allowing long term or permanent expression of any other gene product of interest introduced in the cell by the vector.

In the recombinant parvoviral (rAAV) vectors of the invention the at least one nucleotide sequence(s) encoding a gene product of interest for expression in a mammalian cell, preferably is/are operably linked to at least one mammalian cell-compatible expression control sequence, e.g., a promoter. Many such promoters are known in the art (see Sambrook and Russel, 2001, supra). Contitutive promoters that are broadly expressed in many cell-types, such as the CMV promoter may be used. However, more preferred will be promoters that are inducible, tissue-specific, cell-type-specific, or cell cycle-specific. For example, for liver-specific expression a promoter may be selected from an al-anti-trypsin promoter, a thyroid hormone-binding globulin promoter, an albumin promoter, LPS (thyroxine-binding globlin) promoter, HCR-ApoCII hybrid promoter, HCR-hAAT hybrid promoter and an apolipoprotein E promoter. Other examples include the E2F promoter for tumor-selective, and, in particular, neurological cell tumor-selective expression (Parr et al., 1997, Nat. Med. 3: 1145-9) or the IL-2 promoter for use in mononuclear blood cells (Hagenbaugh et al., 1997, J Exp Med; 185:2101-10).

AAV is able to infect a number of mammalian cells. See, e.g., Tratschin et al. (1985, 30 Mol. Cell Biol. 5:3251-3260) and Grimm et al. (1999, Hum. Gene Tuer. 10:2445-2450). However, AAV transduction of human synovial fibroblasts is significantly more efficient than in similar murine cells, Jennings et al., Arthritis Res, 3:1 (2001), and the cellular tropicity of AAV differs among serotypes. See, e.g., Davidson et al. (2000, Proc. Natl. Acad. Sci. USA, 97:3428-3432), who discuss differences among AAV2, AAV4, and AAV5 with respect to mammalian CNS cell tropism and transduction efficiency.

AAV sequences that may be used in the present invention for the production of recombinant AAV vectors in insect cells can be derived from the genome of any AAV serotype. Generally, the AAV serotypes have genomic sequences of significant homology at the amino acid and the nucleic acid levels, provide an identical set of genetic functions, produce virions which are essentially physically and functionally equivalent, and replicate and assemble by practically identical mechanisms. For the genomic sequence of the various AAV serotypes and an overview of the genomic similarities see e.g. GenBank Accession number U89790; GenBank Accession number J0I90I; GenBank Accession number AF043303; GenBank Accession number AF0857I6; Chlorini et al. (1997, J. Vir. 7I:6823-33); Srivastava et al. (1983, J. Vir. 45:555-64); Chlorini et al. (I999, J. Vir. 73:1309-13I 9); Rutledge et al. (1998, J. Vir. 72:309-3I9); and Wu et al. (2000, J. Vir. 74:8635-47). AAV serotypes I, 2, 3, 4 and 5 are preferred source of AAV nucleotide sequences for use in the context of the present invention. Preferably the AAV ITR sequences for use in the context of the present invention are derived from AAVI, AAV2, and/or AAV4. Likewise, the Rep (Rep78 and Rep52) coding sequences are preferably derived from AAVI, AAV2, and/or AAV4. The sequences coding for the VP1, VP2, and VP3 capsid proteins for use in the context of the present invention may however be taken from any of the known 42 serotypes, more preferably from AAVI, AAV2, AAV3, AAV4, AAVS5, AAV6, AAV7, AAVS or AAV9 or newly developed AAV-like particles obtained by e.g. capsid shuffling techniques and AAV capsid libraries.

AAV Rep and ITR sequences are particularly conserved among most serotypes. The Rep78 proteins of various AAV serotypes are e.g. more than 89% identical and the total nucleotide sequence identity at the genome level between AAV2, AAV3A, AAV3B, and AAV6 is around 82% (Bantel-Schaal et al., 1999, J. Virol., 73(2):939-947). Moreover, the Rep sequences and ITRs of many AAV serotypes are known to efficiently cross-complement (i.e., functionally substitute) corresponding sequences from other serotypes in production of AAV particles in mammalian cells. US2003 I48506 reports that AAV Rep and ITR sequences also efficiently cross-complement other AAV Rep and ITR sequences in insect cells.

The AAV VP proteins are known to determine the cellular tropicity of the AAV virion. The VP protein-encoding sequences are significantly less conserved than Rep proteins and genes among different AAV serotypes. The ability of Rep and ITR sequences to cross-complement corresponding sequences of other serotypes allows for the production of pseudotyped rAAV particles comprising the capsid proteins of a serotype (e.g., AAV3) and the Rep and/or ITR sequences of another AAV serotype (e.g., AAV2). Such pseudotyped rAAV particles are a part of the present invention.

Modified "AAV" sequences also can be used in the context of the present invention, e.g. for the production of rAAV vectors in insect cells. Such modified sequences e.g. include sequences having at least about 70%, at least about 75%, at least about 80%, at least about 85%, at least about 90%, at least about 95%, or more nucleotide and/or amino acid sequence identity (e.g., a sequence having about 75-99% nucleotide sequence identity) to an AAVI, AAV2, AAV3, AAV4, AAV5, AAV6, AAV7, AAVS or AAV9 ITR, Rep, or VP can be used in place of wild-type AAV ITR, Rep, or VP sequences.

Although similar to other AAV serotypes in many respects, AAV5 differs from other human and simian AAV serotypes more than other known human and simian serotypes. In view thereof, the production of rAAV5 can differ from production of other serotypes in insect cells. Where methods of the invention are employed to produce rAAV5, it is preferred that one or more constructs comprising, collectively in the case of more than one construct, a nucleotide sequence comprising an AAV5 ITR, a nucleotide sequence comprises an AAV5 Rep coding sequence (i.e. a nucleotide sequence comprises an AAV5 Rep78). Such ITR and Rep sequences can be modified as desired to obtain efficient production of rAAV5 or pseudotyped rAAV5 vectors in insect cells. E.g., the start codon of the Rep sequences can be modified, VP splice sites can be modified or eliminated, and/or the VP1 start codon and nearby nucleotides can be modified to improve the production of rAAV5 vectors in the insect cell.

In another aspect the invention thus relates to a method for producing a recombinant parvoviral (rAAV) virion (comprising a recombinant parvoviral (rAAV) vector as defined above) in an insect cell. Preferably, the method comprises the steps of: (a) culturing an insect cell as defined in herein above under conditions such that recombinant parvoviral (rAAV) vector is produced; and, (b) recovery of the recombinant parvoviral (rAAV) vector. It is understood here that the recombinant parvoviral (rAAV) vector produced in the method preferably is an infectious parvoviral or AAV virion that comprise the recombinant parvoviral (rAAV) vector nucleic acids. Growing conditions for insect cells in culture, and production of heterologous products in insect cells in culture are well-known in the art and described e.g. in the above cited references on molecular engineering of insects cells.

Preferably the method further comprises the step of affinity-purification of the (virions comprising the) recombinant parvoviral (rAAV) vector using an anti-AAV antibody, preferably an immobilised antibody. The anti-AAV antibody preferably is an monoclonal antibody. A particularly suitable antibody is a single chain camelid antibody or a fragment thereof as e.g. obtainable from camels or llamas (see e.g. Muyldermans, 2001, Biotechnol. 74:277-302). The antibody for affinity-purification of rAAV preferably is an antibody that specifically binds an epitope on a AAV capsid protein, whereby preferably the epitope is an epitope that is present on capsid protein of more than one AAV serotype. E.g. the antibody may be raised or selected on the basis of specific binding to AAV2 capsid but at the same time also it may also specifically bind to AAV1, AAV3 and AAV5 capsids.

In a further aspect the invention relates to a rAAV virion produced in the above described methods of the invention, using the nucleic acid constructs and cells as defined above. Preferably the rAAV virion comprises in its genome at least one nucleotide sequence encoding a gene product of interest, whereby the at least one nucleotide sequence is not a native AAV nucleotide sequence, and whereby in the stoichiometry of the AAV VP1, VP2, and VP3 capsid proteins the amount of VPI: (a) is at least 100, 105, 110, 120, 150, 200 or 400% of the amount of VP2; or (b) is at least 8, 10, 10.5, 11, 12, 15, 20 or 40% of the amount of VP3; or (c) is at least as defined in both (a) and (b). Preferably, the amount of VP1, VP2 and VP3 is determined using an antibody recognising an epitope that is common to each of VPI, VP2 and VP3. Various immunoassays are available in the art that will allow quantify the relative amounts of VPI, VP2 and/or VP3 (see e.g. Using Antibodies, E. Harlow and D. Lane, 1999, Cold Spring Harbor Laboratory Press, New York). An suitable antibody recognising an epitope that is common to each of the three capsid proteins is e.g. the mouse anti-Cap B1 antibody (as is commercially available from Progen, Germany). A preferred rAAV virion according to the invention is a virion comprising in its genome at least one nucleotide sequence encoding a gene product of interest, whereby the at least one nucleotide sequence is not a native AAV nucleotide sequence, and whereby the AAV virion comprises a VP1 capsid protein comprises a leucine or a valine at amino acid position 1. A more preferred AAV virion according to the invention has the ratio's of capsid proteins as defined above and comprises a VP 1 capsid protein comprises a leucine or a valine at amino acid position 1.

In this document and in its claims, the verb "To comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

B) The construct of the invention has the Rep ORF under the control of a single promoter (e.g. the polyhedron (PolH) promoter). This promoter drives the expression of both Rep78 and Rep52 because the Rep78 initiation codon ATG is converted to the alternate ACG initiation codon and partially skipped by the ribosome.

C) The original construct by Urabe et al. (2002, supra) drives Rep78 and Rep52 independently from two different promoters (resp. MEI and polH).

Figure 1:
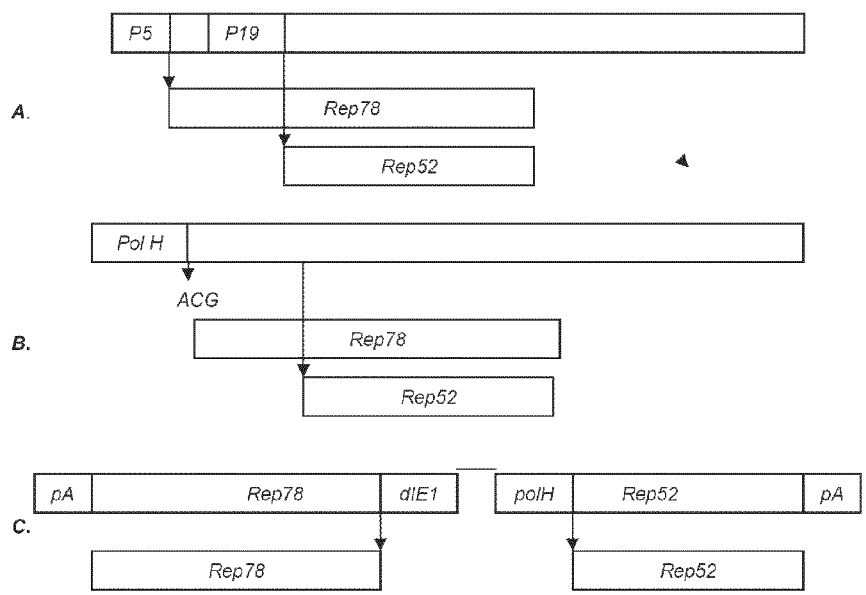
FIG. 1: A) Organisation of Rep expression in the wild type AAV genome. The Rep78 and Rep 52 genes are expressed from respectively the P5 and P19 promoter. Expression of Rep68 and Rep40 (which are the spliced variants of resp. Rep78 and Rep52) are not shown. Both expression units contain a ATG-initiation site.
Figure 2:
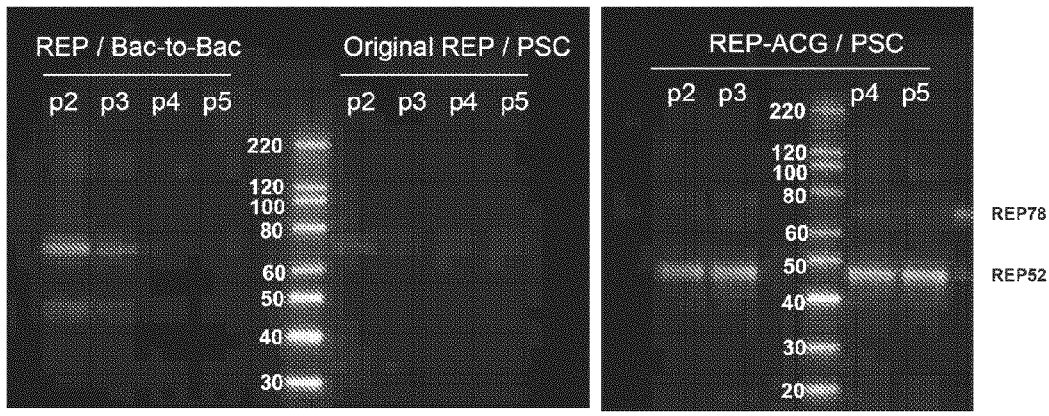
Figure 2:
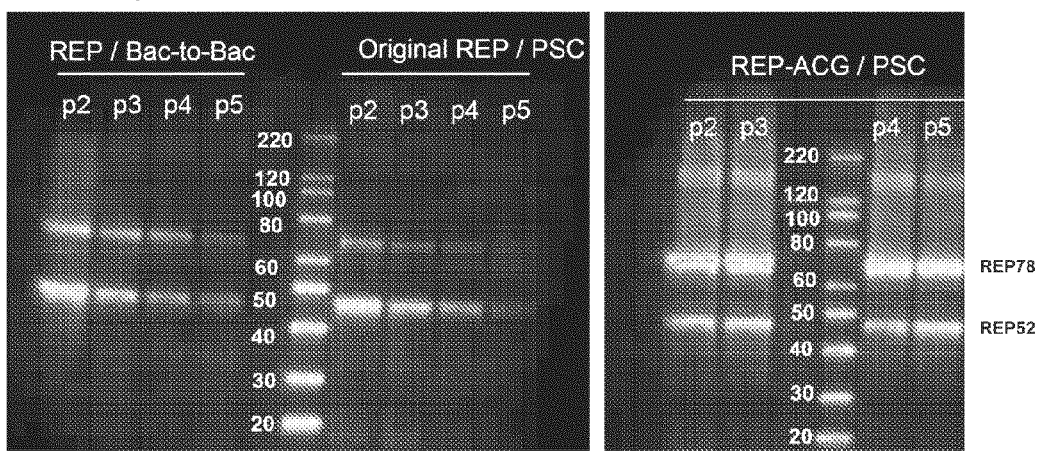
Figure 2:
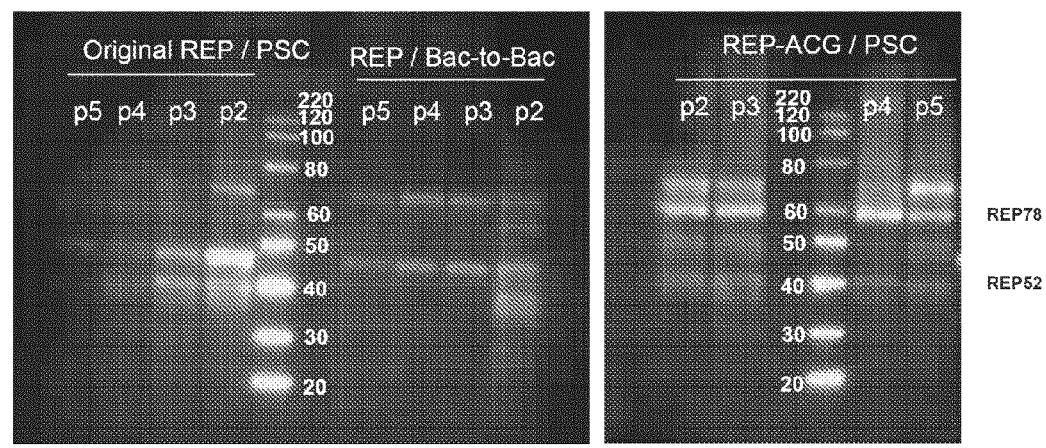

FIG. 2: Western blot analysis of Rep proteins expressed from recombinant baculovirus that was passaged 5 times on insect cells. The original baculovirus designed by Urabe et al., 2002 (original REP/Bae-to-Bae) results in a slow decrease of Rep78/52 expression over 5 passages. The expression unit for Rep78 and 52 designed by Urabe et al., 2002 inserted in baculovirus backbone PSC (original REP I PSC) also results in a decrease of Rep78/52 expression following passaging on insect cells. However, the baculovirus with the REP expression unit containing the ACG initiation codon in the PSC backbone (REP-ACG I PSC) results in stable expression of Rep78/52 over at least 5 passages. Western blot analysis was performed as described in Example 1.1.3.

Figure 3:
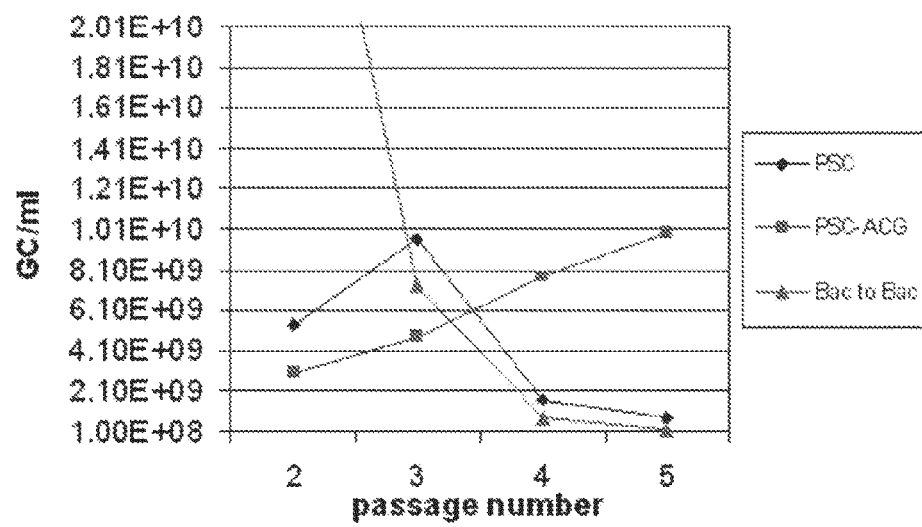

FIG. 3: Results of Table 1 plotted in a graph.

Figure 4:
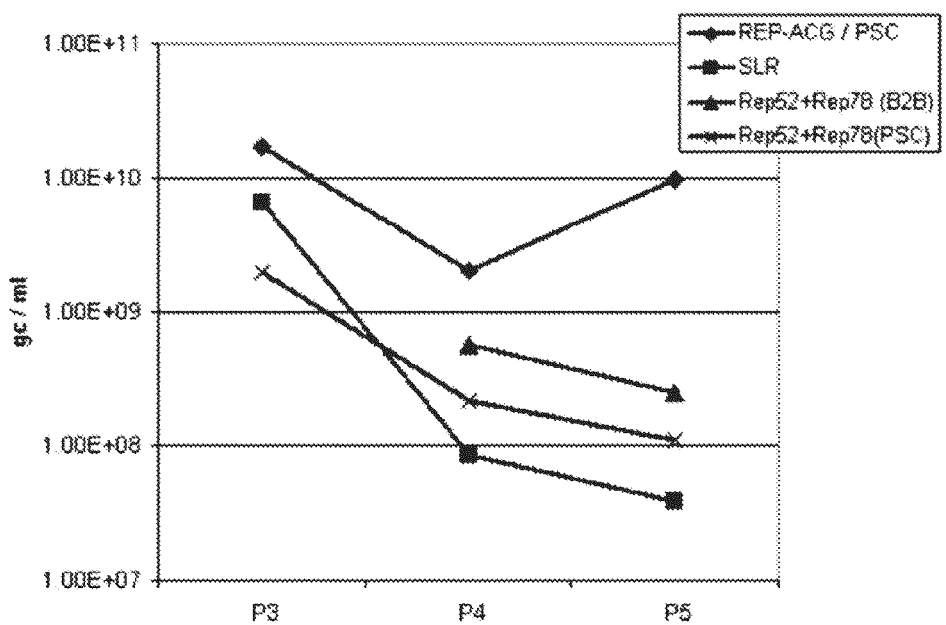

FIG. 4: Comparison of the stabilities of various rAAV constructs in insect cells._rAAV production in SF+ cells was performed as described above in Example 1. For all productions the ITR containing baculovirus and the capsid gene containing baculovirus were identical, the passage number was the same as the Rep gene containing baculoviruses. 4 different Rep gene containing baculoviruses were used: 1) The REP-ACG I PSC, 2) SLR: the original construct by Urabe et al. (2002, supra), 3) Rep52+Rep78(B2B): Two separate Bae-to-Bae baculoviruses, one containing the Rep 78 gene and the other one containing the Rep 52 gene. 4) Rep52+Rep78(PSC): Two separate protein sciences baculoviruses one containing the Rep 78 gene and the other one containing the Rep 52 gene.

Figure 5:
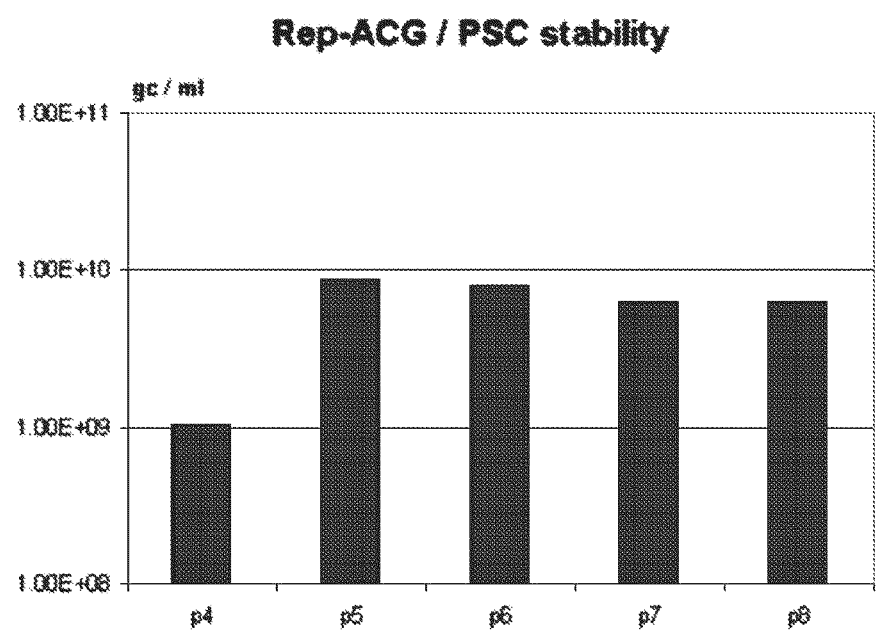

FIG. 5: Stability of the REP-ACG IPSC baculovirus constructs up to passage 8. rAAV productions in SF+ cells were performed as described in Example 1.

Figure 6:
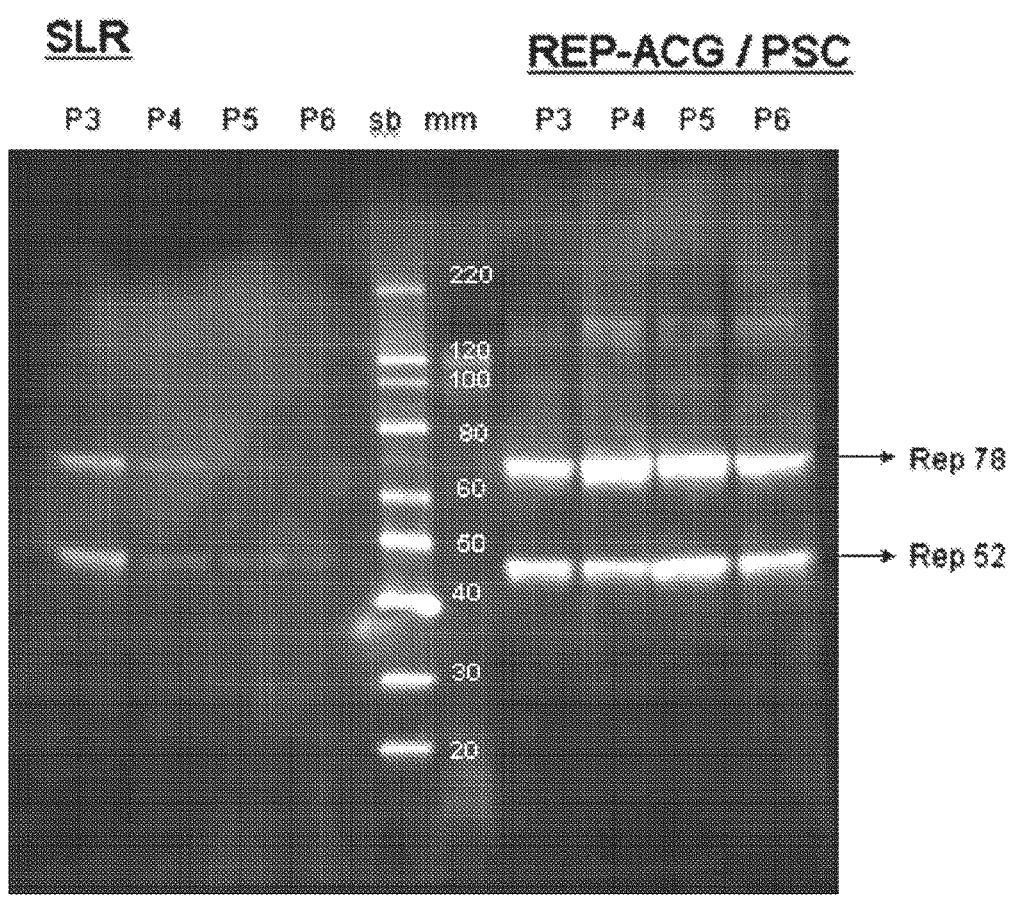

FIG. 6: Comparison of the effect of passage effect on rep protein expression of the original construct from Urabe et al. (2002, supra) with a REP-ACG I PSC construct in accordance with the invention. The baculovirus passages and the western blot were done as described in Example 1. During a normal passage of the rep baculoviruses, samples were taken at 40 hours after addition of the baculoviruses to the SF cells and western blot was performed.

EXAMPLES

Example 1: Rep Constructs 1.1. Materials & Methods 1.1.1 Baculovirus Plasmid Construction In order to express Rep78 and Rep52 from a sole bicistronic messenger RNA, the ATG initiation codon of Rep78 situated on the expression vector pFastBacDualSLR (Urabe et al., 2002, supra) was converted to ACG. The upstream primer used was:

BamHI
(SEQ ID NO. 8)
5'-cgcggatcctgttaagACGGCGGGGTTTTACGAGATTGTGATTAAG
GTC-3'
PRIMER SEQUENCE forward The 3'-primer that was used in the PCR reaction was flanking the REP78 gene and contains a XbaI site (TCTAGA):

```
XbaI
                                       (SEQ ID NO. 9)
5'-AGGCTCTAGATTCGAAAGCGGCCCG-3'
PRIMER SEQUENCE reverse
```

The sequence between the above-mentioned primer set was amplified by PCR (reaction volume 50 µl; Ix Pfx Amp. Buffer, 0.3 mM dNTP's, 1 mM MgSO4, 150 mM primer forw., 150 mM primer rev., 2× enhancer solution, template 50 ng (pFastBacDualSLR), 1 U Platinum Pfx (Invitrogen, Carlsbad, Calif., USA) using the following protocol: 1 cycle of 95° C., 5 min; 35 cycles of 95° C., 15 sec; 55° C., 30 sec; 72° C., 2 min; 1 cycle of 72° C., 10 min; 4° C., for ever). The PCR product was cloned in PCR-blunt II-TOPO using the Zero Blunt TOPO PCR cloning kit (Invitrogen). The Rep78 was subcloned into pFastBacDual (Invitrogen) using the restriction sites SpeI and XbaI. The mutated Rep expression cassette was finally cloned (using restriction enzymes BstZ1 7I and AvrII) into the baculovims expression construct (cut open with EcoRV and XbaI) pPSC1O (Protein Sciences Corporation, Meriden, Conn., USA). The sequence analysis of the construct was verified by Baseclear, Leiden, the Netherlands.

1.1.2 Recombinant Baculovirus Production

Recombinant baculovimses derived from the Autographa californica nuclear polyhydrosis vims (AcNPV) were produced using the GeneXpress BaculoKIT (Protein Sciences Corporation). Transfection was performed as follows: in a round bottom 14 ml tube 200 µl GRACE medium was mixed with 6 µl cellfectine (Invitrogen), and in a eppendorf tube 200 µl GRACE medium was mixed with 50 µl viral DNA (protein sciences) and 2 µg transfer plasmid (REP). The contents from the eppendorf tube were added to the tube and mixed carefully. After an incubation period of 30 minutes at RT 1,300 µl GRACE was added to the transfection mix.

Insect cells in a T25 flask were washed with GRACE medium and the transfection mixture was added dropwise to the cell layer. After an incubation of 6 hours at 28° C. SF900II serum supplemented with 10% FBS was added carefully and the T25 flask was put in a 28° C. stove for 5 days after which the recombinant baculovirus was harvested.

1.1.3 Western Blot Analysis

Insect cells (SF+) were infected with baculovirus-REP. At 16, 40, and 64 hours post-infection cells a sample was taken and cells were lysed by adding O. IV I0×TRIS lysis buffer (1.5M NaCl, 0.5M TRIS, O.OIM MgCl, I % TRITON X-IOO, pH8.5, filter sterilised) and incubated at 28° C. for 30 minutes in a shaker (Innova 44, New Brunswick). Free DNA and RNA was degraded by incubation with benzonase at 37° C. for 30 minutes. Cell lysate was centrifuged (1,900×g; I5 min; 4° C.). NuPAGE LDS sample buffer (4×, Invitrogen) was added to a sample of the supernatant and was loaded onto a 4-12% Bis-Tris gel (120V). Proteins were blotted onto a PVDF membrane (BioRad) for 30 minutes, IOV (Semidry blotting). Western immunochemistry was performed by blocking the membrane with Superblock-PBS blocking buffer (PIERCE) and subsequent incubation with mouse anti-Rep (303.9, Progen, Germany; dilution I:50) and rabbit anti-mouse-HRP (DAKO, dilution I:500). The Rep-proteins were visualized by chemoluminescent staining with lumi-light plus Western-blotting substrate (Roche).

1.2 Results

The performance of the newly designed Rep-construct of the invention (REP-ACG I PSC) was compared with the original Rep constructs in both I) PSC baculovirus backbone and in 2) Bae-to-Bae baculovirus backbone (Urabe et al., 2002). All three constructs were serially passaged until passage 5. AAVI-LPL production experiments were performed using the passage 2, 3, 4 and 5 Rep-constructs in combination with an AAV-LPL and a AAV-Cap recombinant baculovirus of respectively passage 2, 3, 4 and 5 (AAV-LPL and AAV-Cap recombinant Baculovirus used here are described below in Example 2). AAVI-LPL production yields were determined by qPCR and are shown in Table I. The original baculovirus designed by Urabe et al., 2002 (original REP/Bae-to-Bae) results in a fast decrease of AAV production over 5 passages. The expression unit for Rep designed by Urabe et al., 2002 inserted in baculovirus backbone PSC (original REP I PSC) also results in a decrease of AAV production following passaging on insect cells. However, the baculovims with the REP expression unit containing the ACG initiation codon in the PSC backbone (REP-ACG I PSC) results in stable AAV production over at least 5 passages. Therefore, reproducible production yields of AAV-LPL over several passages (e.g. 2 to 5) were only obtained using baculovimses containing the REP-ACG construct.

TABLE 1

Production of rAAV virions using the baculovirus constructs of several passages:

| passage | original REP/ PSC µg/ml | REP-ACG/ PSC µg/ml | original REP/ Bae-to-Bae µg/ml |
|---|---|---|---|
| 2 | 5.38E+09 | 3.04E+09 | 3.62E+10 |
| 3 | 9.57E+09 | 4.77E+09 | 7.28E+09 |
| 4 | 1.66E+09 | 7.81E+09 | 7.59E+08 |
| 5 | 7.35E+08 | 9.90E+09 | 2.03E+08 |

Sf9 cells were infected with three recombinant baculoviruses encoding a LPL-vector unit of passage 2, 3, 4 or 5, a Rep-expression unit of passage 2, 3, 4 or 5 and a Cap-expression unit of passage 2, 3, 4 or 5. After three days cells were harvested and AAV yields (vector genomes per ml; vg/ml) were determined by qPCR.

TABLE 2

Q-PCR performed on the various Bae-Rep constructs following passaging on insect cells (Passage 2-5).

| | titer (gc's/ml) | | | Ratio | Ratio |
|---|---|---|---|---|---|
| | ORF | Rep78 | Rep52 | ORF/Rep7 | ORF/Rep |
| original REP/Bac-to-Bac | 1.4E+09 | 2.2E+08 | 2.4E+08 | 6.42 | 5.82 |
| original REP/Bac-to-Bac | 6.4E+08 | 5.6E+07 | 5.0E+07 | 11.43 | 12.93 |
| original REP/Bac-to-Bac | 2.1E+09 | 7.1E+07 | 6.5E+07 | 29.47 | 32.02 |
| original REP/Bac-to-Bac | 1.7E+09 | 3.2E+07 | 2.5E+07 | 53.68 | 69.67 |

TABLE 2-continued

Q-PCR performed on the various Bae-Rep constructs following passaging on insect cells (Passage 2-5).

|  | titer (gc's/ml) | | | Ratio | Ratio |
|---|---|---|---|---|---|
|  | ORF | Rep78 | Rep52 | ORF/Rep7 | ORF/Rep |
| REP-ACG/PSC (C4) P2 | 3.0E+09 | 2.7E+09 | 2.9E+09 | 1.11 | 1.04 |
| REP-ACG/PSC (C4) P3 | 2.3E+09 | 2.0E+09 | 2.2E+09 | 1.11 | 1.05 |
| REP-ACG/PSC (C4) P4 | 2.5E+09 | 2.2E+09 | 2.3E+09 | 1.13 | 1.08 |
| REP-ACG/PSC (C4) P5 | 2.7E+09 | 2.1E+09 | 2.5E+09 | 1.26 | 1.07 |
| REP-ACG/PSC (A3) P2 | 2.5E+09 | 2.2E+09 | 2.5E+09 | 1.18 | 1.00 |
| REP-ACG/PSC (A3) P3 | 4.2E+09 | 3.9E+09 | 4.0E+09 | 1.08 | 1.04 |
| REP-ACG/PSC (A3) P4 | 2.7E+09 | 2.4E+09 | 2.5E+09 | 1.10 | 1.05 |
| REP-ACG/PSC (A3) P5 | 1.5E+09 | 1.5E+09 | 1.5E+09 | 1.03 | 0.98 |
| original REP/Bae-to-Bae | 1.0E+09 | 1.1E+09 | 1.1E+09 | 0.95 | 0.87 |
| original REP/Bae-to-Bae | 7.1E+08 | 6.7E+08 | 8.1E+08 | 1.07 | 0.88 |
| original REP/Bae-to-Bae | 1.3E+08 | 1.1E+08 | 1.3E+08 | 1.18 | 1.03 |
| original REP/Bae-to-Bae | 1.3E+08 | 5.3E+07 | 6.9E+07 | 2.34 | 1.82 |

Table 2 shows the results of a quantitative PCR (Q-PCR) assay that was designed for the Rep-expression unit in the recombinant baculoviruses and for a flanking baculovirus ORF (gene copies per ml; gc's/ml). The ratio between the Q-PCR values determines the presence of deletions in the Rep-baculovirus. A ratio of I theoretically means that all baculoviruses in the batch contain a recombinant Rep78 or 52-sequence. The original baculovirus designed by Urabe et al., 2002 (original REP/Bae-to-Bae) shows significant amounts of the recombinant baculovirus at passage 5 have deletions in the Rep sequences. The expression unit for Rep78 and 52 designed by Urabe et al., 2002 inserted in baculovirus backbone PSC (original REP I PSC) shows a very early and dramatic loss of recombinant baculovirus. However, the baculovirus with the REP expression unit containing the ACG initiation codon in the PSC backbone (REP-ACG/PSC) (clone C4 and A3) show stable recombinant baculoviruses over at least 5 passages.

Example 2: Cap Constructs 2.1.1 Baculovims Plasmid Construction

In order to express VPI, 2, 3 from a sole polycistronic messenger RNA, the baculovims-AAV-Cap construct was designed as described by (Urabe et al., 2002, supra). Briefly, the ATG initiation codon of VPI was mutated to ACG. A potential ATG initiation codon at position I I has been changed to ACG. The splice acceptor site downstream of the VPI initiation codon was destroyed (mutation at position 2I and 24). The mutated Cap expression cassette was cloned into a baculovims expression construct; pFastBacDual (pFBDAAVIVPmI I) with BamH1/StuI restriction sites. This plasmid (pFBDAAVIVPmI I) was the starting material for introduction of alternate initiation codons for VPI. The forward primer used by Urabe et al. (2002, supra) in order to introduce the mentioned mutations was:

```
BamHI
                                        (SEQ ID NO. 1)
                  1      11      21 24
5'-cgcggat cctgttaagACGGCTGCCGACGGTTATCTACCCGATTG

GCTC-3'
```

The following forward primers were used to make the expression constructs using pFBDAAVIVPmI I (Urabe et al., 2002, supra) as starting material:

```
                                        (SEQ ID NO. 2)
5'-cgcggat cctgttaagTTGGCTGCCGACGGTTATCTACCCGATTG

GCTC-3'

(SEQ ID NO. 3)
5'-cgcggatcctgttaagATTGCTGCCGACGGTTATCTACCCGATTGG

CTC-3'

(SEQ ID NO. 4)
5'-cgcggatcctgttaagGTGGCTGCCGACGGTTATCTACCCGATTGG

CTC-3'
                                        (SEQ ID NO. 5)
5'-cgcggatcctgttaagCTGGCTGCCGACGGTTATCTACCCGATTGG

CTC-3'
```

The backward-primer that was used in the PCR reactions with the above forward primers was directed to position 230 bp downstream of the VPI initiation codon and contains a unique Stu I site (AGGCCT).

```
                                        (SEQ ID NO. 6)
         5'-GTCGTAGGCCTTGTCGTGCTCGAGGGCCGC-3'
```

Fragments were amplified with the above-mentioned sets of forward and backward primer pairs by PCR. Following digestion of PCR products with BamHI and StuI the PCR products were subcloned into the BamHI/StuI sites of pFBDAAVIvpmI I resulting in the various to be tested baculovirus-AAV-Cap constructs. DNA constructs were verified by sequence analysis at Baseclear, Leiden, the Netherlands.

2.1.2 Recombinant Baculovirus Production

Recombinant baculoviruses derived from the Autographa californica nuclear polyhydrosis virus (AcNPV) were produced using the Bae-to-Bae baculovirus expression system (Invitrogen). rBac-Cap was amplified by infecting $2\times10^6$ Sf9 cells per ml at an moi of 0.1. Three days after infection the cells were spun down and the supernatant containing the virus recovered.

2.1.3 Recombinant AAV Production rAAV batches were produced using three recombinant baculoviruses according to Urabe et al., 2002. However, for this study one baculovirus harboured an expression construct for the $LPL^{s447x}$-transgene. The therapeutically active agent expressed from the transgene is a naturally occurring variant of human lipoprotein lipase, a single chain polypeptide of 448 amino acids.

The $LPL^{s447x}$ variant has a deletion of two amino acids at the C-terminus of the protein. The second baculovirus harboured an expression construct for the AAV replication genes, Rep 78 and Rep 52. The third baculovirus harboured the AAVI capsid sequence with either an ACG or a TTG, CTG, GTG initiation codon for VPI.

Mammalian-rAAV batches produced with the plasmid-transfection system were produced according to Grimm et al., 1998 (Novel tools for production and purification of recombinant adeno-associated virus vectors. Hum Gene Ther. 1998 December 10; 9(18):2745-60).

2.1.3 Western Blot Analysis

Insect cells were infected with baculovirus-Cap. At three days post-infection cells were centrifuged (3,000 g; 15 min). The supernatant was filtered through a 0.22 um Millex filter. NuPAGE LDS sample buffer (Invitrogen) was added to a sample of the supernatant and was loaded onto a 4-12% Bis-Tris gel. The gel was run at 100V. Proteins were blotted onto a nitrocellulose membrane (BioRad) for 1 hr, 100V, 350 mA. Western immunochemistry was performed by blocking the membrane with 1 % marvel, dried skimmed milk and subsequently incubation with mouse anti-Cap (BI from Progen, Germany; dilution 1:50) and rabbit anti-mouse-HRP (DAKO, dilution 1:100). VP 1, 2 and 3 were visualized by chemoluminescent staining with lumi-light plus Western-blotting substrate (Roche).

2.1.4 Biochemical Measurements

Human $LPL^{s447x}$ activity was assayed as previously described using a radioactive trioleoylglycerol emulsion substrate (Nilsson-Ehle and Scholtz, 1976). Human $LPL^{s447x}$ immunoreactive mass was assayed using a sandwich ELISA with chicken IgY and mouse 5D2 anti-hLPL antibodies (Liu et al., 2000). Plasma triglyceride levels were measured by using commercial kits following manufacturer protocols (Boehringer Mannheim, #450032).

2.2 Results

2.2.1 Construction of Recombinant Baculovirus

In order to introduce different alternate initiation codons for VP1 expression in the baculovirus plasmid designed by Urabe et al. (2002, supra) a series of upstream primers were designed containing a BamHI restriction site and either a TTG, ATT, GTG or CTG codon in place of the ACG initiation codon of VPI.PCR using these primers in combination with a downstream primer containing a StuI site resulted in amplified fragments that were subcloned into the BamHVStuI site of pFBDVPml 1 (Bae-Cap). The resulting baculovirus plasmids were used for the preparation of recombinant baculovimses using the Bae-to-Bae baculovirus expression system. The prepared recombinant baculovimses were infected on insect cells in order to produce AAV capsids. At three days following infection viral protein expression of the different baculovirus batches were determined on Western blots. From the Western blots it became clear that the baculovirus construct containing the TTG initiation codon for VP1 expressed this protein to a higher level compared to the previously used ACG initiation codon. The ratio between VP1 and VP2 using the TTG codon was found to be 1:1 which is similar to what is reported for wild type AAV (not shown).

2.2.2 Infection of rAAV Batches on Cells in Culture

In order to investigate the infectivity of the AAV capsids derived from recombinant baculovimses with the TTG initiation codon rAAV was generated. Also a rAAV batch was generated by plasmid transfection on mammalian HEK293 cells. A vector genome titer of both rAAV batches was determined by qPCR. This titer was used to infect HEK 293 cells in a microtiter plate at an increasing moi. At two days following infection an quantitative assay ($LPL^{s447x}$-mass assay) for the transgene product ($LPL^{s447x}$) was performed on the medium of the infected cells. The assay showed that the amount of $LPL^{s447x}$ produced by baculovirus-produced rAAV was similar to the LPL produced by the plasmid-produced rAAV (not shown).

2.2.3 Injection of rAAV Batches in Mice

The rAAV batches produced with the baculovirus-production system and with the conventional mammalian plasmid-production system were injected intramuscularly in mice to follow $LPL^{s447x}$_protein activity and triglyceride fasting in vivo. At 3 days, 7 days and at 2 weeks following injection blood samples were taken and evaluated. Between 3 and 7 days post virus administration blood-plasma sampled from both mice injected with mammalian-rAAV and one mouse injected with baculo-rAAV was turned from milky to completely clear. Blood plasma derived from one baculo-rAAV-injected mouse remained relatively milky however fat level was clearly reduced. Triglyceride levels were lowered respectively of all treated mice (not shown). On day 14 TG levels in both mammalian-AAV and baculovirus-(TTG)-AAV treated mice TG levels were reduced for 96%. Plasma samples taken at two weeks after virus administration showed that the $LPL^{s447x}$-activity of the mice treated with baculovirus-AAV and mammalian-AAV was similar (not shown).

Example 3: Stability of RAAV Contructs with Modified Rep 78 Initiation Codon in Insect Cells

3.1 Comparison of the Stabilities of Various rAAV Constructs in Insect Cells rAAV productions in SF+ cells were performed as described above in Example 1. For all productions the ITR containing baculovirus and the capsid gene containing baculovirus were identical, the passage number was the same as the Rep gene containing baculoviruses. 4 different Rep gene containing baculovirus were used: 1) The REP-ACG/PSC, 2) SLR: the original construct by Urabe et al. (2002, supra), 3) Rep52+Rep78(B2B): Two separate Bae-to-Bae baculoviruses, one containing the Rep 78 gene and the other one containing the Rep 52 gene. 4) Rep52+Rep78(PSC): Two separate protein sciences baculoviruses one containing the Rep 78 gene and the other one containing the Rep 52 gene.

Results are shown in FIG. 4 at fifth baculovirus passage rAAV production is already improved by more than a factor 10 using a REP-ACG/PSC in accordance with invention as compared to the original Rep construct and compared to the split Rep constructs.

3.2 Stability of the Baculovirus Constructs Up to Passage 8 rAAV productions in SF+ cells were performed as described in Example 1. For all productions the ITR containing baculovirus and the capsid gene containing baculovirus were identical, the passage number was the same as the REP-ACG/PSC baculovirus. Results are shown in FIG. 5. The REP-ACG/PSC baculovirus is stable to at least passage 8. rAAV production titers of REP-ACG/PSC are stable up to at least 8th passage of the baculovirus.

3.3 Passage Effect on Rep Protein Expression

The effect of passage number on the expression of Rep protein for the original construct from Urabe et al. (2002, supra) was compared to a REP-ACG I PSC construct in accordance with the invention. The baculovirus passages and the western blot were done as described in Example 1. During a normal passage of the rep baculovirsues, samples were taken at 40 hours after addition of the baculovirsues to the SF cells and western blot was performed. FIG. 6 clearly shows diminished Rep expression in higher passages compared to earlier passages for the original Urabe construct (SLR), while the Rep expression in the REP-ACG/PSC construct stays the same in the higher passages compared to the lower ones.

The invention claimed is:

1. A method of producing a recombinant parvoviral virion in an insect cell comprising, transfecting an insect cell with a nucleotide sequence encoding parvoviral Rep proteins Rep78 and Rep52, the nucleotide sequence comprising a Rep78 coding sequence and a Rep52 coding sequence, the Rep78 coding sequence and the Rep52 coding sequence being operably linked to expression control sequences for expression of both a Rep78 protein and a Rep52 protein in an insect cell; wherein the Rep52 coding sequence is comprised within the Rep78 coding sequence, and wherein the nucleotide sequence is stably maintained within the insect cell over at least 5 passages.

2. The method of claim 1, wherein the Rep78 and Rep52 are expressed over at least 5 passages of the insect cell.

3. The method of claim 1, wherein Rep78 and Rep52 are produced in a molar ratio in the range of 1:10 to 10:1.

4. The method of claim 1, wherein the nucleotide sequence is comprised within a nucleic acid construct.

5. The method of claim 4, wherein the nucleic acid construct is comprised within a baculovirus vector.

6. The method of claim 1, wherein the insect cell is selected from the group consisting of Se301, Seizd2109, Seucr1, sf9, Sf900+, Sf21, Bti-Tn-5b1-4, Mg-1, Tn368, Hzam1, Ha2302, Hz2e5, High five and Express+.

7. The method of claim 6, wherein the insect cell is sf9.

8. The method of claim 1, wherein the nucleotide sequence is stably maintained within the insect cell over at least 8 passages.

9. A method of producing a recombinant parvoviral virion in an insect cell comprising, transfecting an insect cell with a nucleic acid construct encoding parvoviral Rep proteins Rep78 and Rep52, the nucleic acid construct comprising:
   (a) a bicistronic nucleic acid encoding a parvovirus Rep78 protein and a parvovirus Rep52 protein, wherein the nucleic acid sequence encoding the Rep78 protein overlaps the nucleic acid sequence encoding the Rep52 protein, such that the nucleic acid sequence encoding the parvoviral Rep52 protein is not repeated in the bicistronic nucleic acid;
   (b) a first expression control sequence that comprises an initiation codon and is active in an insect cell operably linked to the sequence encoding Rep78 protein;
   (c) a second expression control sequence that is active in an insect cell operably linked to the sequence encoding Rep52 protein;
   wherein both the parvoviral Rep78 protein and the parvoviral Rep52 protein are produced over at least 5 passages of the insect cell when the nucleic acid construct is expressed by the insect cell.

10. The method of claim 9, wherein the nucleic acid construct is stably maintained within the insect cell over at least 5 passages.

11. The method of claim 9, wherein the parvoviral Rep78 protein and the parvoviral Rep52 protein are produced in a molar ratio in the range of 1:10 to 10:1.

12. The method of claim 9, wherein the nucleic acid construct is comprised within a baculovirus vector.

13. The method of claim 9, wherein the insect cell is selected from the group consisting of Se301, Seizd2109, Seucr1, sf9, Sf900+, Sf21, Bti-Tn-5b1-4, Mg-1, Tn368, Hzam1, Ha2302, Hz2e5, High five and Express+.

14. The method of claim 9, wherein the insect cell is sf9.

15. The method of claim 9, wherein the nucleotide acid construct is stably maintained within the insect cell over at least 8 passages.

* * * * *

SEQUENCE LISTING

```
<160> NUMBER OF SEQ ID NOS: 11

<210> SEQ ID NO 1
<211> LENGTH: 49
<212> TYPE: DNA
<213> ORGANISM: artificial sequence
<220> FEATURE:
<223> OTHER INFORMATION: primer

<400> SEQUENCE: 1
cgcggatcct gttaagacgg ctgccgacgg ttatctaccc gattggctc          49

<210> SEQ ID NO 2
<211> LENGTH: 49
<212> TYPE: DNA
<213> ORGANISM: artificial sequence
<220> FEATURE:
<223> OTHER INFORMATION: primer

<400> SEQUENCE: 2
cgcggatcct gttaagttgg ctgccgacgg ttatctaccc gattggctc          49

<210> SEQ ID NO 3
<211> LENGTH: 49
<212> TYPE: DNA
<213> ORGANISM: artificial sequence
<220> FEATURE:
<223> OTHER INFORMATION: primer

<400> SEQUENCE: 3
cgcggatcct gttaagattg ctgccgacgg ttatctaccc gattggctc          49

<210> SEQ ID NO 4
<211> LENGTH: 49
<212> TYPE: DNA
<213> ORGANISM: artificial sequence
<220> FEATURE:
<223> OTHER INFORMATION: primer

<400> SEQUENCE: 4
cgcggatcct gttaaggtgg ctgccgacgg ttatctaccc gattggctc          49

<210> SEQ ID NO 5
<211> LENGTH: 49
<212> TYPE: DNA
<213> ORGANISM: artificial sequence
<220> FEATURE:
<223> OTHER INFORMATION: primer
```

-continued

```
<400> SEQUENCE: 5
cgcggatcct gttaagctgg ctgccgacgg ttatctaccc gattggctc        49

<210> SEQ ID NO 6
<211> LENGTH: 30
<212> TYPE: DNA
<213> ORGANISM: artificial sequence
<220> FEATURE:
<223> OTHER INFORMATION: primer

<400> SEQUENCE: 6
gtcgtaggcc ttgtcgtgct cgagggccgc                             30

<210> SEQ ID NO 7
<211> LENGTH: 9
<212> TYPE: DNA
<213> ORGANISM: Adeno-associated virus 2

<400> SEQUENCE: 7 cctgttaag                                                     9

<210> SEQ ID NO 8
<211> LENGTH: 49
<212> TYPE: DNA
<213> ORGANISM: Artificial sequence
<220> FEATURE:
<223> OTHER INFORMATION: primer

<400> SEQUENCE: 8
cgcggatcct gttaagacgg cggggttttta cgagattgtg attaaggtc       49

<210> SEQ ID NO 9
<211> LENGTH: 25
<212> TYPE: DNA
<213> ORGANISM: Artificial sequence
<220> FEATURE:
<223> OTHER INFORMATION: primer

<400> SEQUENCE: 9
aggctctaga ttcgaaagcg gcccg                                  25

<210> SEQ ID NO 10
<211> LENGTH: 1876
<212> TYPE: DNA
<213> ORGANISM: adeno-associated virus 2
<220> FEATURE:
<221> NAME/KEY: CDS
<222> LOCATION: (11)..(1876)
<223> OTHER INFORMATION: Rep 78
<220> FEATURE:
<221> NAME/KEY: CDS
<222> LOCATION: (683)..(1876)
<223> OTHER INFORMATION: Rep52

<400> SEQUENCE: 10
cgcagccgcc atg ccg ggg ttt tac gag att gtg att aag gtc ccc agc    49
            Met Pro Gly Phe Tyr Glu Ile Val Ile Lys Val Pro Ser
              1               5                  10 gac ctt gac gag cat ctg ccc ggc att tct gac agc ttt gtg aac tgg   97
Asp Leu Asp Glu His Leu Pro Gly Ile Ser Asp Ser Phe Val Asn Trp
     15                  20                  25 gtg gcc gag aag gaa tgg gag ttg ccg cca gat tct gac atg gat ctg  145
Val Ala Glu Lys Glu Trp Glu Leu Pro Pro Asp Ser Asp Met Asp Leu
 30              35                  40                  45
```

```
aat ctg att gag cag gca ccc ctg acc gtg gcc gag aag ctg cag cgc      193
Asn Leu Ile Glu Gln Ala Pro Leu Thr Val Ala Glu Lys Leu Gln Arg
            50                  55                  60 gac ttt ctg acg gaa tgg cgc cgt gtg agt aag gcc ccg gag gcc ctt      241
Asp Phe Leu Thr Glu Trp Arg Arg Val Ser Lys Ala Pro Glu Ala Leu
        65                  70                  75 ttc ttt gtg caa ttt gag aag gga gag agc tac ttc cac atg cac gtg      289
Phe Phe Val Gln Phe Glu Lys Gly Glu Ser Tyr Phe His Met His Val
    80                  85                  90 ctc gtg gaa acc acc ggg gtg aaa tcc atg gtt ttg gga cgt ttc ctg      337
Leu Val Glu Thr Thr Gly Val Lys Ser Met Val Leu Gly Arg Phe Leu
95                  100                 105 agt cag att cgc gaa aaa ctg att cag aga att tac cgc ggg atc gag      385
Ser Gln Ile Arg Glu Lys Leu Ile Gln Arg Ile Tyr Arg Gly Ile Glu
110                 115                 120                 125 ccg act ttg cca aac tgg ttc gcg gtc aca aag acc aga aat ggc gcc      433
Pro Thr Leu Pro Asn Trp Phe Ala Val Thr Lys Thr Arg Asn Gly Ala
            130                 135                 140 gga ggc ggg aac aag gtg gtg gat gag tgc tac atc ccc aat tac ttg      481
Gly Gly Gly Asn Lys Val Val Asp Glu Cys Tyr Ile Pro Asn Tyr Leu
        145                 150                 155 ctc ccc aaa acc cag cct gag ctc cag tgg gcg tgg act aat atg gaa      529
Leu Pro Lys Thr Gln Pro Glu Leu Gln Trp Ala Trp Thr Asn Met Glu
    160                 165                 170 cag tat tta agc gcc tgt ttg aat ctc acg gag cgt aaa cgg ttg gtg      577
Gln Tyr Leu Ser Ala Cys Leu Asn Leu Thr Glu Arg Lys Arg Leu Val
175                 180                 185 gcg cag cat ctg acg cac gtg tcg cag acg cag gag cag aac aaa gag      625
Ala Gln His Leu Thr His Val Ser Gln Thr Gln Glu Gln Asn Lys Glu
190                 195                 200                 205 aat cag aat ccc aat tct gat gcg ccg gtg atc aga tca aaa act tca      673
Asn Gln Asn Pro Asn Ser Asp Ala Pro Val Ile Arg Ser Lys Thr Ser
            210                 215                 220 gcc agg tac atg gag ctg gtc ggg tgg ctc gtg gac aag ggg att acc      721
Ala Arg Tyr Met Glu Leu Val Gly Trp Leu Val Asp Lys Gly Ile Thr
        225                 230                 235 tcg gag aag cag tgg atc cag gag gac cag gcc tca tac atc tcc ttc      769
Ser Glu Lys Gln Trp Ile Gln Glu Asp Gln Ala Ser Tyr Ile Ser Phe
    240                 245                 250 aat gcg gcc tcc aac tcg cgg tcc caa atc aag gct gcc ttg gac aat      817
Asn Ala Ala Ser Asn Ser Arg Ser Gln Ile Lys Ala Ala Leu Asp Asn
255                 260                 265 gcg gga aag att atg agc ctg act aaa acc gcc ccc gac tac ctg gtg      865
Ala Gly Lys Ile Met Ser Leu Thr Lys Thr Ala Pro Asp Tyr Leu Val
270                 275                 280                 285 ggc cag cag ccc gtg gag gac att tcc agc aat cgg att tat aaa att      913
Gly Gln Gln Pro Val Glu Asp Ile Ser Ser Asn Arg Ile Tyr Lys Ile
            290                 295                 300 ttg gaa cta aac ggg tac gat ccc caa tat gcg gct tcc gtc ttt ctg      961
Leu Glu Leu Asn Gly Tyr Asp Pro Gln Tyr Ala Ala Ser Val Phe Leu
        305                 310                 315 gga tgg gcc acg aaa aag ttc ggc aag agg aac acc atc tgg ctg ttt     1009
Gly Trp Ala Thr Lys Lys Phe Gly Lys Arg Asn Thr Ile Trp Leu Phe
    320                 325                 330 ggg cct gca act acc ggg aag acc aac atc gcg gag gcc ata gcc cac     1057
Gly Pro Ala Thr Thr Gly Lys Thr Asn Ile Ala Glu Ala Ile Ala His
335                 340                 345 act gtg ccc ttc tac ggg tgc gta aac tgg acc aat gag aac ttt ccc     1105
Thr Val Pro Phe Tyr Gly Cys Val Asn Trp Thr Asn Glu Asn Phe Pro
350                 355                 360                 365
```

```
ttc aac gac tgt gtc gac aag atg gtg atc tgg tgg gag gag ggg aag    1153
Phe Asn Asp Cys Val Asp Lys Met Val Ile Trp Trp Glu Glu Gly Lys
                370                 375                 380 atg acc gcc aag gtc gtg gag tcg gcc aaa gcc att ctc gga gga agc    1201
Met Thr Ala Lys Val Val Glu Ser Ala Lys Ala Ile Leu Gly Gly Ser
            385                 390                 395 aag gtg cgc gtg gac cag aaa tgc aag tcc tcg gcc cag ata gac ccg    1249
Lys Val Arg Val Asp Gln Lys Cys Lys Ser Ser Ala Gln Ile Asp Pro
        400                 405                 410 act ccc gtg atc gtc acc tcc aac acc aac atg tgc gcc gtg att gac    1297
Thr Pro Val Ile Val Thr Ser Asn Thr Asn Met Cys Ala Val Ile Asp
    415                 420                 425 ggg aac tca acg acc ttc gaa cac cag cag ccg ttg caa gac cgg atg    1345
Gly Asn Ser Thr Thr Phe Glu His Gln Gln Pro Leu Gln Asp Arg Met
430                 435                 440                 445 ttc aaa ttt gaa ctc acc cgc cgt ctg gat cat gac ttt ggg aag gtc    1393
Phe Lys Phe Glu Leu Thr Arg Arg Leu Asp His Asp Phe Gly Lys Val
                450                 455                 460 acc aag cag gaa gtc aaa gac ttt ttc cgg tgg gca aag gat cac gtg    1441
Thr Lys Gln Glu Val Lys Asp Phe Phe Arg Trp Ala Lys Asp His Val
            465                 470                 475 gtt gag gtg gag cat gaa ttc tac gtc aaa aag ggt gga gcc aag aaa    1489
Val Glu Val Glu His Glu Phe Tyr Val Lys Lys Gly Gly Ala Lys Lys
        480                 485                 490 aga ccc gcc ccc agt gac gca gat ata agt gag ccc aaa cgg gtg cgc    1537
Arg Pro Ala Pro Ser Asp Ala Asp Ile Ser Glu Pro Lys Arg Val Arg
    495                 500                 505 gag tca gtt gcg cag cca tcg acg tca gac gcg gaa gct tcg atc aac    1585
Glu Ser Val Ala Gln Pro Ser Thr Ser Asp Ala Glu Ala Ser Ile Asn
510                 515                 520                 525 tac gca gac agg tac caa aac aaa tgt tct cgt cac gtg ggc atg aat    1633
Tyr Ala Asp Arg Tyr Gln Asn Lys Cys Ser Arg His Val Gly Met Asn
                530                 535                 540 ctg atg ctg ttt ccc tgc aga caa tgc gag aga atg aat cag aat tca    1681
Leu Met Leu Phe Pro Cys Arg Gln Cys Glu Arg Met Asn Gln Asn Ser
            545                 550                 555 aat atc tgc ttc act cac gga cag aaa gac tgt tta gag tgc ttt ccc    1729
Asn Ile Cys Phe Thr His Gly Gln Lys Asp Cys Leu Glu Cys Phe Pro
        560                 565                 570 gtg tca gaa tct caa ccc gtt tct gtc gtc aaa aag gcg tat cag aaa    1777
Val Ser Glu Ser Gln Pro Val Ser Val Val Lys Lys Ala Tyr Gln Lys
    575                 580                 585 ctg tgc tac att cat cat atc atg gga aag gtg cca gac gct tgc act    1825
Leu Cys Tyr Ile His His Ile Met Gly Lys Val Pro Asp Ala Cys Thr
590                 595                 600                 605 gcc tgc gat ctg gtc aat gtg gat ttg gat gac tgc atc ttt gaa caa    1873
Ala Cys Asp Leu Val Asn Val Asp Leu Asp Asp Cys Ile Phe Glu Gln
                610                 615                 620 taa                                                                 1876

<210> SEQ ID NO 11
<211> LENGTH: 621
<212> TYPE: PRT
<213> ORGANISM: adeno-associated virus 2

<400> SEQUENCE: 11

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
```

-continued

```
            20                  25                  30
Lys Glu Trp Glu Leu Pro Pro Asp Ser Asp Met Asp Leu Asn Leu Ile
            35                  40                  45
Glu Gln Ala Pro Leu Thr Val Ala Glu Lys Leu Gln Arg Asp Phe Leu
    50                  55                  60
Thr Glu Trp Arg Arg Val Ser Lys Ala Pro Glu Ala Leu Phe Phe Val
65                  70                  75                  80
Gln Phe Glu Lys Gly Glu Ser Tyr Phe His Met His Val Leu Val Glu
                85                  90                  95
Thr Thr Gly Val Lys Ser Met Val Leu Gly Arg Phe Leu Ser Gln Ile
            100                 105                 110
Arg Glu Lys Leu Ile Gln Arg Ile Tyr Arg Gly Ile Glu Pro Thr Leu
        115                 120                 125
Pro Asn Trp Phe Ala Val Thr Lys Thr Arg Asn Gly Ala Gly Gly Gly
    130                 135                 140
Asn Lys Val Val Asp Glu Cys Tyr Ile Pro Asn Tyr Leu Leu Pro Lys
145                 150                 155                 160
Thr Gln Pro Glu Leu Gln Trp Ala Trp Thr Asn Met Glu Gln Tyr Leu
                165                 170                 175
Ser Ala Cys Leu Asn Leu Thr Glu Arg Lys Arg Leu Val Ala Gln His
            180                 185                 190
Leu Thr His Val Ser Gln Thr Gln Glu Gln Asn Lys Glu Asn Gln Asn
        195                 200                 205
Pro Asn Ser Asp Ala Pro Val Ile Arg Ser Lys Thr Ser Ala Arg Tyr
    210                 215                 220
Met Glu Leu Val Gly Trp Leu Val Asp Lys Gly Ile Thr Ser Glu Lys
225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Gly Lys
            260                 265                 270
Ile Met Ser Leu Thr Lys Thr Ala Pro Asp Tyr Leu Val Gly Gln Gln
        275                 280                 285
Pro Val Glu Asp Ile Ser Ser Asn Arg Ile Tyr Lys Ile Leu Glu Leu
    290                 295                 300
Asn Gly Tyr Asp Pro Gln Tyr Ala Ala Ser Val Phe Leu Gly Trp Ala
305                 310                 315                 320
Thr Lys Lys Phe Gly Lys Arg Asn Thr Ile Trp Leu Phe Gly Pro Ala
                325                 330                 335
Thr Thr Gly Lys Thr Asn Ile Ala Glu Ala Ile Ala His Thr Val Pro
            340                 345                 350
Phe Tyr Gly Cys Val Asn Trp Thr Asn Glu Asn Phe Pro Phe Asn Asp
        355                 360                 365
Cys Val Asp Lys Met Val Ile Trp Trp Glu Glu Gly Lys Met Thr Ala
    370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Asp Pro Thr Pro Val
                405                 410                 415
Ile Val Thr Ser Asn Thr Asn Met Cys Ala Val Ile Asp Gly Asn Ser
            420                 425                 430
Thr Thr Phe Glu His Gln Gln Pro Leu Gln Asp Arg Met Phe Lys Phe
        435                 440                 445
```

```
Glu Leu Thr Arg Arg Leu Asp His Asp Phe Gly Lys Val Thr Lys Gln
    450                 455                 460
Glu Val Lys Asp Phe Phe Arg Trp Ala Lys Asp His Val Val Glu Val
465                 470                 475                 480
Glu His Glu Phe Tyr Val Lys Lys Gly Gly Ala Lys Lys Arg Pro Ala
                485                 490                 495
Pro Ser Asp Ala Asp Ile Ser Glu Pro Lys Arg Val Arg Glu Ser Val
            500                 505                 510
Ala Gln Pro Ser Thr Ser Asp Ala Glu Ala Ser Ile Asn Tyr Ala Asp
        515                 520                 525
Arg Tyr Gln Asn Lys Cys Ser Arg His Val Gly Met Asn Leu Met Leu
    530                 535                 540
Phe Pro Cys Arg Gln Cys Glu Arg Met Asn Gln Asn Ser Asn Ile Cys
545                 550                 555                 560
Phe Thr His Gly Gln Lys Asp Cys Leu Glu Cys Phe Pro Val Ser Glu
                565                 570                 575
Ser Gln Pro Val Ser Val Val Lys Lys Ala Tyr Gln Lys Leu Cys Tyr
            580                 585                 590
Ile His His Ile Met Gly Lys Val Pro Asp Ala Cys Thr Ala Cys Asp
        595                 600                 605
Leu Val Asn Val Asp Leu Asp Asp Cys Ile Phe Glu Gln
610                 615                 620
```